US008164050B2

(12) United States Patent
Ford et al.

(10) Patent No.: US 8,164,050 B2
(45) Date of Patent: Apr. 24, 2012

(54) MULTI-CHANNEL SOURCE ASSEMBLY FOR DOWNHOLE SPECTROSCOPY

(75) Inventors: Jess V. Ford, Weatherford, TX (US); Thomas Blankinship, Fort Worth, TX (US); Bryan W. Kasperski, Crowley, TX (US); Margaret C. Waid, Aledo, TX (US); Sean M. Christian, Land O Lakes, FL (US)

(73) Assignee: Precision Energy Services, Inc., Fort Worth, TX (US)

( * ) Notice: Subject to any disclaimer, the term of this patent is extended or adjusted under 35 U.S.C. 154(b) by 132 days.

(21) Appl. No.: 12/613,700

(22) Filed: Nov. 6, 2009

(65) Prior Publication Data
US 2011/0108719 A1 May 12, 2011

(51) Int. Cl.
G01V 5/04 (2006.01)
(52) U.S. Cl. ..................... 250/262; 250/269.1
(58) Field of Classification Search ............... 250/269.1
See application file for complete search history.

(56) References Cited

U.S. PATENT DOCUMENTS

| 3,941,483 | A | 3/1976 | Ferrin |
| 4,264,205 | A | 4/1981 | Landa |
| 4,285,596 | A | 8/1981 | Landa |
| 4,412,744 | A | 11/1983 | Lee et al. |
| 4,692,621 | A | 9/1987 | Passaro et al. |
| 4,785,806 | A | 11/1988 | Deckelbaum |
| 4,832,490 | A | 5/1989 | Boos |
| 4,962,815 | A | 10/1990 | Schultz et al. |
| 4,968,148 | A | 11/1990 | Chow |
| 4,994,671 | A | 2/1991 | Safinya et al. |
| 5,128,797 | A | 7/1992 | Sachse et al. |
| 5,166,747 | A | 11/1992 | Schroeder et al. |
| 5,167,149 | A | 12/1992 | Mullins et al. |
| 5,170,056 | A | 12/1992 | Berard |
| 5,173,808 | A | 12/1992 | Auer et al. |
| 5,257,086 | A | 10/1993 | Fateley et al. |
| 5,337,621 | A | 8/1994 | Spease |
| 5,371,543 | A | 12/1994 | Anderson |
| 5,401,966 | A | 3/1995 | Gray et al. |
| 5,440,118 | A | 8/1995 | Roscoe |
| 5,475,221 | A | 12/1995 | Wang |
| 5,504,575 | A | 4/1996 | Stafford |

(Continued)

FOREIGN PATENT DOCUMENTS
WO 81/00775 3/1981
(Continued)

OTHER PUBLICATIONS

European Search Report for Application No. EP 10188545, dated Feb. 14, 2011.

(Continued)

Primary Examiner — David Porta
Assistant Examiner — Hugh H Maupin
(74) Attorney, Agent, or Firm — Wong, Cabello, Lutsch, Rutherford & Brucculeri, LLP

(57) ABSTRACT

A multi-channel source assembly for downhole spectroscopy has individual sources that generate optical signals across a spectral range of wavelengths. A combining assembly optically combines the generated signals into a combined signal and a routing assembly that splits the combined signal into a reference channel and a measurement channel. Control circuitry electrically coupled to the sources modulates each of the sources at unique or independent frequencies during operation.

50 Claims, 12 Drawing Sheets

U.S. PATENT DOCUMENTS

| | | | |
|---|---|---|---|
| 5,557,398 | A | 9/1996 | Wechsler et al. |
| 5,629,125 | A | 5/1997 | Leblans et al. |
| 5,825,478 | A | 10/1998 | Wilcox |
| 5,828,066 | A | 10/1998 | Messerschmidt |
| 5,859,430 | A | 1/1999 | Mullins et al. |
| 5,966,484 | A * | 10/1999 | Yuuki .......................... 385/43 |
| 6,064,488 | A | 5/2000 | Brand et al. |
| 6,075,595 | A | 6/2000 | Malinen |
| 6,128,078 | A | 10/2000 | Fateley |
| 6,301,959 | B1 | 10/2001 | Hrametz et al. |
| 6,420,695 | B1 | 7/2002 | Grasdepot |
| 6,429,936 | B1 | 8/2002 | Scaduto |
| 6,437,326 | B1 * | 8/2002 | Yamate et al. ............. 250/269.1 |
| 6,465,775 | B2 | 10/2002 | Mullins et al. |
| 6,476,384 | B1 | 11/2002 | Mullins et al. |
| 6,504,943 | B1 | 1/2003 | Sweatt et al. |
| 6,559,945 | B1 | 5/2003 | Grasdepot |
| 6,571,118 | B1 | 5/2003 | Utzinger et al. |
| 6,600,591 | B2 | 7/2003 | Anderson et al. |
| 6,678,050 | B2 | 1/2004 | Pope et al. |
| 6,693,701 | B2 | 2/2004 | Hansen |
| 6,753,960 | B1 | 6/2004 | Polynkin et al. |
| 6,768,105 | B2 | 7/2004 | Mullins et al. |
| 6,781,691 | B2 | 8/2004 | MacKinnon et al. |
| 6,798,518 | B2 | 9/2004 | DiFoggio et al. |
| 6,870,619 | B1 | 3/2005 | Tenhunen et al. |
| 6,939,717 | B2 | 9/2005 | Jiang |
| 6,995,360 | B2 | 2/2006 | Jones et al. |
| 7,013,723 | B2 | 3/2006 | Ramakrishnan et al. |
| 7,265,830 | B2 | 9/2007 | Wang |
| 7,279,678 | B2 | 10/2007 | Andrews et al. |
| 7,280,214 | B2 | 10/2007 | DiFoggio et al. |
| 7,321,428 | B2 | 1/2008 | Hunt |
| 7,336,356 | B2 | 2/2008 | Vannuffelen et al. |
| 7,360,924 | B2 | 4/2008 | Henson et al. |
| 7,362,422 | B2 | 4/2008 | DiFoggio et al. |
| 7,379,180 | B2 | 5/2008 | Vannuffelen |
| 7,403,680 | B2 | 7/2008 | Simbal |
| 7,609,380 | B2 | 10/2009 | Vannuffelen et al. |
| 7,782,389 | B2 * | 8/2010 | Neidrich ........................ 348/340 |
| 7,782,460 | B2 * | 8/2010 | DiFoggio et al. ............. 356/409 |
| 2003/0206026 | A1 | 11/2003 | Diakonov et al. |
| 2004/0069942 | A1 | 4/2004 | Fujisawa et al. |
| 2004/0149915 | A1 | 8/2004 | Goncalves |
| 2004/0169858 | A1 | 9/2004 | Da Silva |
| 2004/0201850 | A1 | 10/2004 | Hajian et al. |
| 2004/0239923 | A1 | 12/2004 | Adams et al. |
| 2004/0239931 | A1 | 12/2004 | Teichmann et al. |
| 2005/0185179 | A1 | 8/2005 | Wang |
| 2005/0243312 | A1 | 11/2005 | Geshwind et al. |
| 2005/0275844 | A1 | 12/2005 | Kaltenbacher |
| 2006/0243033 | A1 | 11/2006 | Freemark et al. |
| 2007/0013911 | A1 | 1/2007 | DiFoggio |
| 2007/0035737 | A1 | 2/2007 | Andrews et al. |
| 2007/0109537 | A1 | 5/2007 | Vannuffelen |
| 2007/0159625 | A1 | 7/2007 | DiFoggio |
| 2007/0171412 | A1 | 7/2007 | Vannuffelen |
| 2007/0171414 | A1 | 7/2007 | Vannuffelen |
| 2007/0229821 | A1 | 10/2007 | Christian et al. |
| 2008/0078544 | A1 | 4/2008 | Christian et al. |
| 2008/0087078 | A1 | 4/2008 | Vannuffelen |
| 2008/0165356 | A1 | 7/2008 | DiFoggio et al. |
| 2008/0173083 | A1 | 7/2008 | Kasperski et al. |
| 2008/0174777 | A1 | 7/2008 | Carron |
| 2010/0067844 | A1 * | 3/2010 | Sanders ........................ 385/12 |

FOREIGN PATENT DOCUMENTS

| | | |
|---|---|---|
| WO | 95/04263 | 2/1995 |

OTHER PUBLICATIONS

Cantrell, "The SLIM Spectrometer" Anal. Chem. 2003, 75, pp. 27-35, Department of Chemistry, Oregon State University, 153 Gilbert Hall, Corvallis, Oregon 97331-4001.

Hauser, "A Multi-Wavelength Photometer Based on Light-Emitting Diodes" Talanta, vol. 42, No. 4, pp. 605-612, 1995.

Keranen, "Analytic and Raytrace Modeling of a Miniaturized Infrared Spectrometer Module".

Malinen et al., Sensors and Actuators B 51 (1998) 220-224,"LED-based NIR spectrometer module for hand-held and process analyser applications," dated Jun. 16, 1998.

O'Toole, "Absorbance Based Light Emitting Diode Optical Sensors and Sensing Devices," *Sensors* 2008, 8, pp. 2453-2479; dated Apr. 7, 2008 obtained from www.mdpi.org/sensors.

Palma, "Portable light-emitting diode-based photometer with one-shot optochemical sensors for measurement in the field," dated Oct. 21, 2008, American Institute of Physics.

Schlumberger, "Fundamentals of Formation Testing," © 2006, pp. 1-5, 27-29, 55-67, 99-124, 199-202, Schlumberger Marketing Communications, Sugar Land, Texas, United States.

Schlumberger, "Engineering the Next-Generation Downhole Fluid Analysis Tool," dated May 7, 2007.

OZ Optics, "Silicon Optical Bench Platforms," dated Nov. 14, 2002, obtained from www.ozoptics.com.

Yeh, "A Low Cost LED Based Spectrometer," Journal of the Chinese Chemical Society, 2006, 53, pp. 1067-1072.

Thorlabs Inc., "Stepped Circular Neutral Density Filter," Drawing No. 10661-E01, Part No. NDC-100S-4.

Thorlabs Inc., "Mounted Round Step Variable NDC Filter," Drawing No. 10664-E01, Part No. NDC-100S-4M.

Frentress, "Field Photometer with Nine-Element Filter Wheel," dated Feb. 1964, vol. 3, No. 2, Applied Optics, pp. 303-308.

International Search Report and Written Opinion received in corresponding Application No. PCT/US07/82221, dated May 5, 2008.

International Search Report, International Patent Application No. PCT/US07/080112, mailed on Mar. 25, 2008.

Dudley, Dana, et al., "Emerging Digital Micromirror Device (DMD) Applications," DLP Products New Applications, Texas Instruments, Inc. undated.

Wagner, Eugene P. II, et al., "Construction and Evaluation of a Visible Spectrometer Using Digital Micromirror Spatial Light Modulation," Applied Spectroscopy, vol. 49, No. 11, 1995.

Ford, Joseph E., et al., "Dynamic Spectral Power Equalization Using Micro-Opto-Mechanics," IEEE Photonics Technology Letters, vol. 10, No. 10, Oct. 1998.

Duncan, Walter M., "Dynamic Optical Filtering in DWDM Systems Using the DMD," Solid State Electronics 46 (2002), pp. 1583-1585.

Lerner, J.M., et al., "The Optics of Spectroscopy—A Tutorial," Instruments SA, Inc., 1988.

Spudich, Thomas M., et al., "Potential for using a Digital Micromirror Device as a Signal Multiplexer in Visible Spectrscopy," Applied Spectroscopy, vol. 57, No. 7, 2003.

DeVerse, R. A., et al, "Realization of the Hadamard Multiplex Advantage Using a Programmable Optical Mask in a Dispersive Flat-Field Near-Infrared Spectrometer," Applied Spectroscopy, vol. 54, No. 12, 2000.

Badry, R., et al., "Downhole Optical Analysis of Formation Fluids," Oilfield Review, Jan. 1994.

Schroeder, R., "Slick Engineering," Spie's OE Magazine, May 2003.

Raghuraman, B., "Real-Time Downhold pH Measurement Using Optical Spectroscopy," SPE 93057, Society of Petroleum Engineers, 2005.

Sirkis, J., "Multifunctionality the Key in Challenging Instrumentation Markets," Lightwave Magazine, Mar. 2003.

Meyer, R., "RITMOS: A Micromirror-Based Multi-Object Spectrometer," Proceedings of the SPIE, 2004.

Smits, A.R., "In-Situ Optical Fluid Analysis as an Aid to Wireline Formation Sampling," SPE Formation Evaluation, Jun. 1995.

Texas Instruments, Application Report, "Single Panel DLP Projection System Optics," Mar. 2005.

Texas Instruments, Product Preview, "DMD 0.7 XGA 12.degree. LVDS DMD Discovery," Jul. 2005.

Texas Instruments, Product Preview Data Sheet, "DMD 0.7 XGA 12.degree. DDR DMD Discovery," Aug. 30, 2005.

Texas Instruments, "DMD Discovery 1100 Chip Set," 2004.

Texas Instruments, "DMD Discovery 3000 Digital Controller (DDC3000) Starter Kit Technical Reference Manual," Oct. 2005.

Texas Instruments, "DMD Discovery 1100 Controller Board and Starter Kit," Oct. 2004.

Texas Instruments, "DMD Discovery 1100 Controller Board GUI User's & Programmer's Guide," Sep. 2004.

Baker Hughes, "RCI Reservoir Characterization Instrument," obtained from www.bakerhughesdirect.com, generated on Apr. 8, 2010.

Baker Hughes, "SampleView" 2000, obtained from www.bakerhughesdirect.com, generated on Apr. 19, 2010.

First Examination Report in counterpart Australian Appl. No. 20100227020, dated Jul. 22, 2011.

First Examination Report in counterpart Australian Appl. No. 2010227019, dated Jul. 22, 2011.

First Office Action in co-pending U.S. Appl. No. 12/613,665, mailed Aug. 26, 2011.

Reply to First Office Action mailed Aug. 26, 2011 in co-pending U.S. Appl. No. 12/613,665, filed Nov. 28, 2011.

* cited by examiner

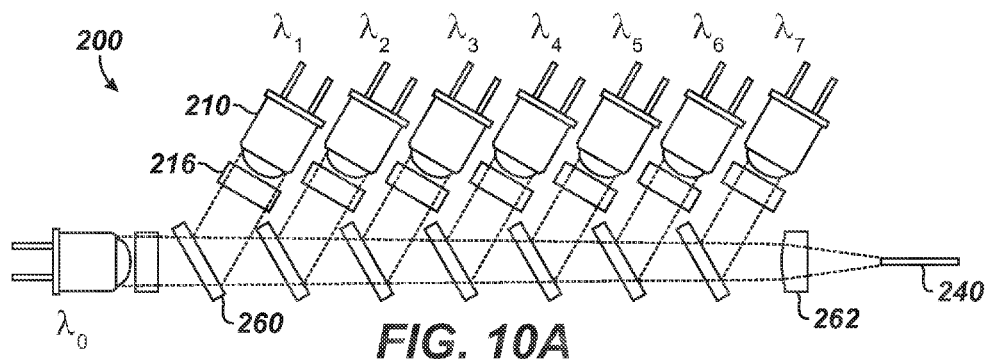
FIG. 10A
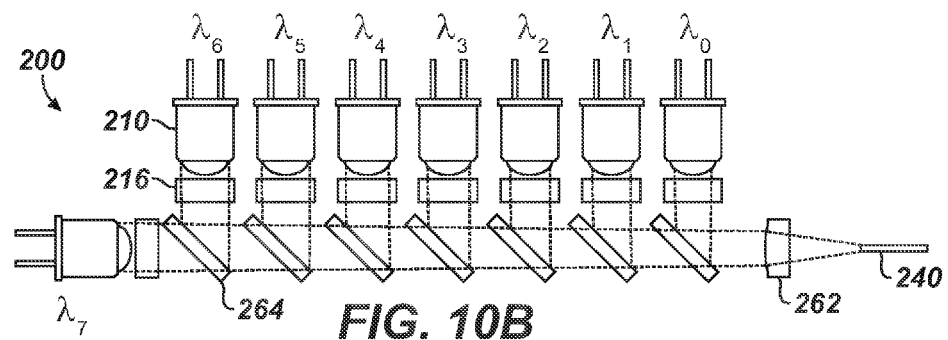
FIG. 10B
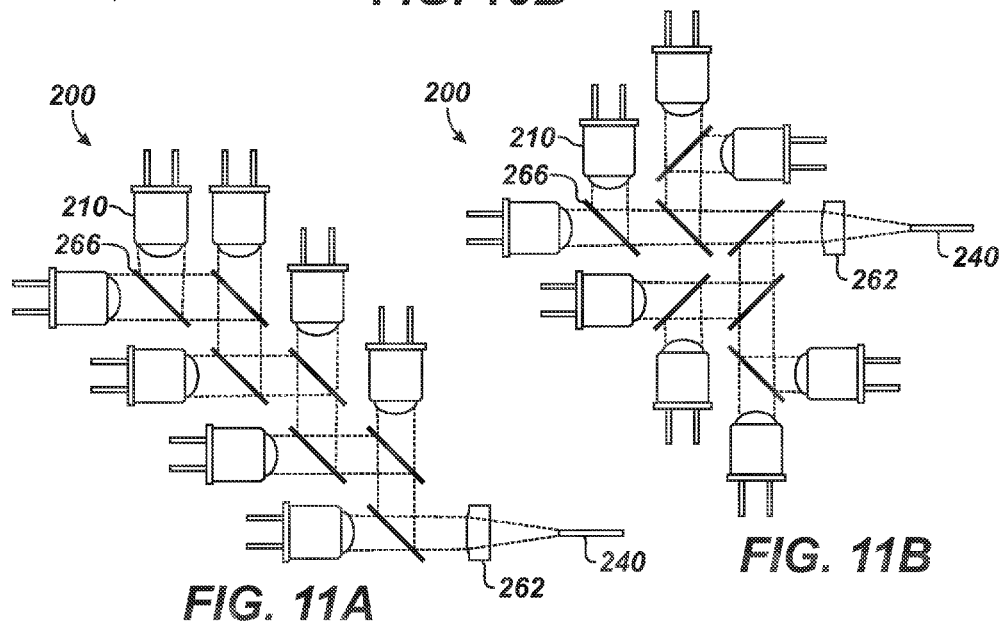
FIG. 11A
FIG. 11B

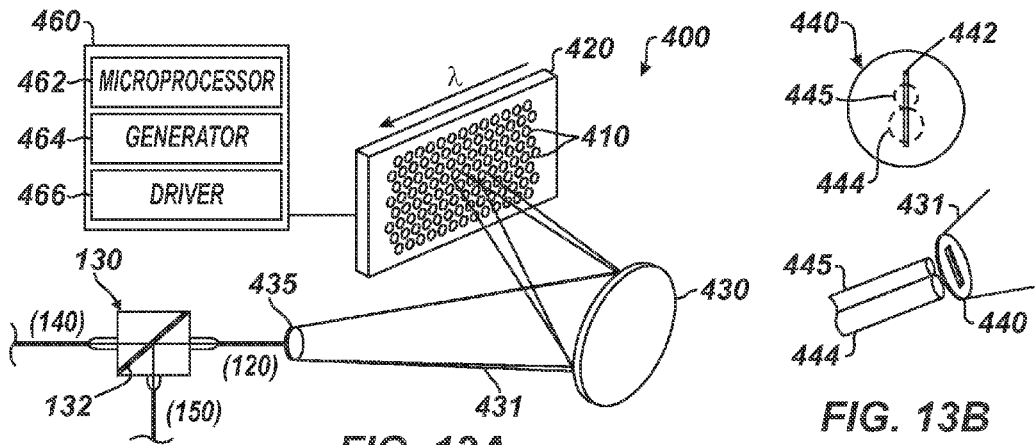
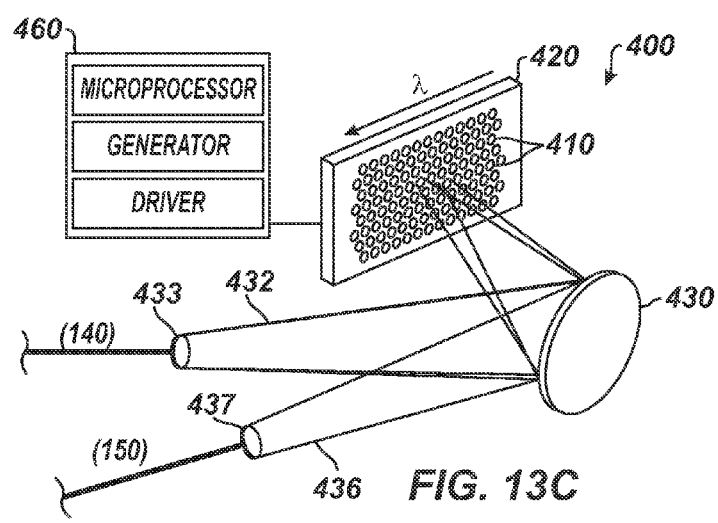
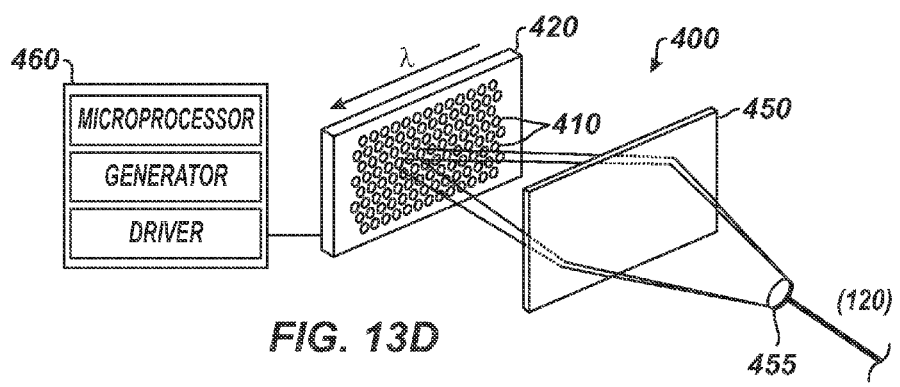

MULTI-CHANNEL SOURCE ASSEMBLY FOR DOWNHOLE SPECTROSCOPY

CROSS-REFERENCE TO RELATED APPLICATIONS

This application is filed concurrently with application Ser. No. 12/613,808 and entitled "Multi-Channel Detector Assembly for Downhole Spectroscopy", and with application Ser. No. 12/613,665 and entitled "Filter Wheel Source Assembly for Downhole Spectroscopy," which are both incorporated herein by reference in their entireties.

BACKGROUND

Downhole tools use various types of sensors to test a downhole formation, analyze fluids, and perform other operations. Because the downhole environment has high temperatures, high pressures, harsh chemicals, and mechanical vibrations, the downhole tools must be mechanically designed to handle problems associated with such harsh conditions, and the downhole sensors must be able to operate with analytical accuracy and reliability. Added to these challenges, the downhole sensors must fit in the limited space available in the downhole environment, must be light weight and power efficient, and have a large dynamic range.

In the art, spectrophotometers, spectrometers, spectrofluorometers, refractive index analyzers, and similar devices have been used to analyze downhole fluids by measuring the fluid's spectral response. Each of these device typically use some form of EM radiation to perform its function (i.e., to analyze the fluid). In general, the wavelengths of the EM radiation can be in the x-ray, gamma, ultraviolet, visible, infrared or any combination of these ranges. When the radiation is detected, the response can identify characteristics of the analyzed fluid, such as the type of fluid (e.g., oil, water, and/or gas), the level of filtrate contamination, the hydrocarbon composition (e.g., amount of methane (C1), ethane (C2), propane (C3), etc.), the gas-to-oil ratio (GOR), etc. Knowledge of these characteristics can then be employed to model the reservoir, plan production, and perform other tasks.

A number of optical devices have been developed in the art for spectral analysis. For example, a spectrometer disclosed in U.S. Pat. No. 6,075,595 is based on light emitting diodes (LEDs) and is capable of imaging into a single optical channel. See also Malinen et al., "LED-based NIR Spectrometer Module for Hand-Held and Process Analyser Applications," Sensors & Actuators B, vol. 51, no. (1-3), pp. 220-226 (1998). In another example, a multi-wavelength photometer uses seven LEDs, 1-mm plastic optic fibers, a 7×2 coupler, and two photodiodes. See Hauser et al., "A Multi-wavelength Photometer Based on Light-Emitting Diodes," Talanta, vol. 42, no. 4, pp. 605-612 (1995). Still other small spectroscopes also use LEDs. See Cantrell et al., "The SLIM Spectrometer," Analytical Chemistry, vol. 75, no. 1, pp. 27-35 (2003); See also Yeh et al., "Low Cost LED Based Spectrometer," Journal of the Chinese Chemical Society, vol. 53, pp. 1067-1072 (2006). None of these devices is suitable for use in a downhole environment due to the harsh temperature and pressure requirements in the borehole environment.

Other devices disclosed in the art can be used downhole. In U.S. Pat. No. 6,476,384 to Mullins et al., for example, a device has a broadband halogen lamp source and has a mechanical chopper wheel driven by a motor. The lamp is imaged into an optical fiber bundle, and light from the bundle is directed to a photodiode used to synchronize the chopper wheel's motor. A calibration wheel driven by a rotary solenoid switch selects whether light from the bundle passes into a first path, a second path, or both. In the first path, light is directed to a light distributor forming part of a detector. In the second path, light is provided as input to a measurement cell and is afterward directed to the light distributor for the detector. The light distributor distributes the light received from the paths to a number of different channels with each channel having a lens, a bandpass filter, and a photodiode. While this device's broadband source does provide a number of spectral channels, the device must use a mechanical chopper, cannot perform synchronous detection, and requires a complex spectral detection system consisting of multiple photodiodes (i.e., one per spectral channel).

In U.S. Pat. Nos. 7,336,356 and 7,379,180 to Vannuffelen et al., a device has a broadband source. The device uses a rotating chopper wheel rotated by a motor to modulate the frequency of reference and measurement paths independently. For example, the measurement path has a first frequency and is split into two parts, and the reference path has a second frequency and is split into two parts. Each of these parts is then routed to multiple detection systems.

In US Pat. Pub. No. 2007/0109537, Vannuffelen et al. discloses an alternative approach that utilizes mechanical choppers and motors. Unfortunately, this approach, by design, is apparently limited to conventional raster scanning (CRS) spectroscopy, which involves scanning a plurality of sources or measurement wavelengths in a sequential fashion using a fixed time per channel (i.e. source or wavelength). As a consequence, CRS prevents synchronous detection of all spectral channels. Moreover, the device requires reference and measurement signals to be de-convolved using a single detector. Because the signal convolution using a single mechanical chopper results in shared harmonics, the device uses dual mechanical chopper assemblies to circumvent the complication of shared harmonics. Although this may simplify signal de-convolution, it adds further complexity to the devices and raises concerns relative to space, mechanical reliability, and accuracy.

Another device for downhole analysis of fluids disclosed in US Pat. Pub. No. 2007/0013911 to DiFoggio et al. provides Wavelength Modulation Spectroscopy (WMS). The device uses a narrow light beam source and a tunable optical filter (TOF). In additional disclosures of U.S. Pat. Nos. 7,280,214 and 7,362,422, both electrically tunable filters and mechanically (i.e. rotating) tunable filters are used for WMS. As purported, WMS eliminates the need for a second spectral reference channel. However, the devices have limited spectral range, which limits their use for downhole analysis of fluids. Specifically, each filter, whether electrical or mechanical in nature, possesses a limited tunable spectral bandwidth. To increase spectral range, the device requires multiple narrow band sources and tunable filters, which are mechanically cumbersome for the downhole environment. In addition, the device uses a single channel detection system that prohibits synchronous detection because the tunable optical filters are actuated using a single motor assembly, which gives each spectral channel a common fundamental frequency.

As disclosed in US Pat. Pub. No. 2008/0165356 to DiFoggio et al., another device has a laser diode array source containing a plurality of semiconductor light sources that enable conventional raster scanning (CRS) and Hadamard and synchronous Fast-Fourier Transform (FFT) scanning. However, the device lacks a way to dynamically scale the spectral response, and the device's sources lack a way for imaging a large number of spectral channels into a single spectral analyzer.

Therefore, in light of the above, what is lacking in the art is a viable broadband multi-channel source for downhole spectral analysis that enables self referencing, low-power operation, synchronous detection, and S/N improvement using discreet modulation of individual spectral channels.

SUMMARY

A multi-channel source assembly can be used in a downhole tool to provide optical signals for downhole spectroscopy. The source assembly has individual sources that generate optical signals across a spectral range of wavelengths. A combiner assembly optically combines the generated signals into a combined signal, and then a routing assembly routes the combined signal into a reference channel and a measurement channel. Control circuitry electrically coupled to the sources can modulate each of the sources at a unique or independent frequency during operation.

The control circuitry can include a plurality of inputs and outputs for external control of the sources. This external control can be manual or automated and can be received from surface equipment or a downhole controller. When provided, the external control can operate the source assembly to account for variable conditions, such as a change in temperature, a change in desired mode of operation, etc. Also, the external control can operate the source assembly to handle events that require exact timing by triggering signals both in and out of the circuitry. An automated scheme for controlling the source assembly can use amplitude measurements of the reference channel. These measurements can be delivered to the source control circuitry from an external detection assembly to detect optical signals of the reference channel and to provide sensed signals as feedback to the source control circuitry. In turn, the source control circuitry can use the feedback to control the individual sources.

In one implementation, the routing assembly has one or more couplers optically coupled to each of the sources and has a router optically coupled to the couplers to split the combined signals into the reference and measurement channels. The couplers can be optical fibers—each having one of the sources imaged therein. Each of the fibers can then bundle together into a fiber bundle optically coupled to a router. Alternatively, the fibers can be fused with one another using a tree topology. In another alternative, the coupler can be a segmented mirror having the sources arranged thereabout. This segmented mirror can image optical signals from each of the sources to at least one fiber optic cable optically coupled to the router. In still another alternative, the couplers can be a series of filters disposed adjacent the sources that image at least a portion of the optical signals from each of the adjacent sources to the same fiber optical cable.

In one implementation, the routing assembly (also referred to as a router) has a splitter fractionally splitting the combined signal from the sources into the reference and measurement channels. Alternatively, the router can be an adaptive optical element or scanning optic that oscillates between two or more orientations. The scanning optic in the first orientation produces the reference channel, whereas the scanning optic in the second orientation produces the measurement channel. Although the scanning optic asynchronously images the reference and measurement channels, the scanning optic can provide an enhanced signal throughput, especially if it is run at a substantially lower frequency relative to the modulation of the individual optical channels.

In one implementation, the sources are spatially configured on an array, and the routing assembly can be a transmissive or reflective grating optically coupled to the spatially configured sources. The grating can combine the generated signals from the sources into a common optical beam that is then imaged using a router into a reference channel and a measurement channel. Alternatively, the reference channel can be picked off at the image point of the grating assembly using a second optical fiber for the reference channel. However, in a preferred embodiment, the measurement channel is imaged using the first order reflection of the grating, and the reference channel is imaged using the second order reflection of the grating, thereby removing the requirement of a router assembly and improving spectral efficiency of the source assembly.

In operation, the control circuitry controls the sources by electronically modulating the sources. In general, the control circuitry can operate all of the sources simultaneously, a subset of the sources simultaneously, or each source individually. For example, the control circuitry can operate the sources in a synchronous encoding mode in which each of two or more sources are operated simultaneously and modulated with a unique frequency to generate optical signals. Alternatively, the control circuitry can operate the sources in an asynchronous encoding mode in which each of two or more sources are operated in a serial fashion with only one source on at any point in time. Moreover, the sources can be operated in an asynchronous Hadamard Transform encoding mode in which a unique sequence of a subset of the sources is operated in a cyclic fashion with only one subset of the sources in operation at a given point in time.

BRIEF DESCRIPTION OF THE DRAWINGS

FIGS. 10A-10B illustrate bulk coupling assemblies having a series of source and filters imaging optical signals into a single optical channel.

FIGS. 11A-11B illustrate additional bulk coupling assemblies having a non-linear arrangement of sources and filters imaging optical signals into a single optical channel.

FIGS. 13A-13D illustrate beam coupling assemblies that use an array of sources and a grating.

DETAILED DESCRIPTION

A. Downhole Tool Having Measurement Device for Fluid Analysis

Figure 1:
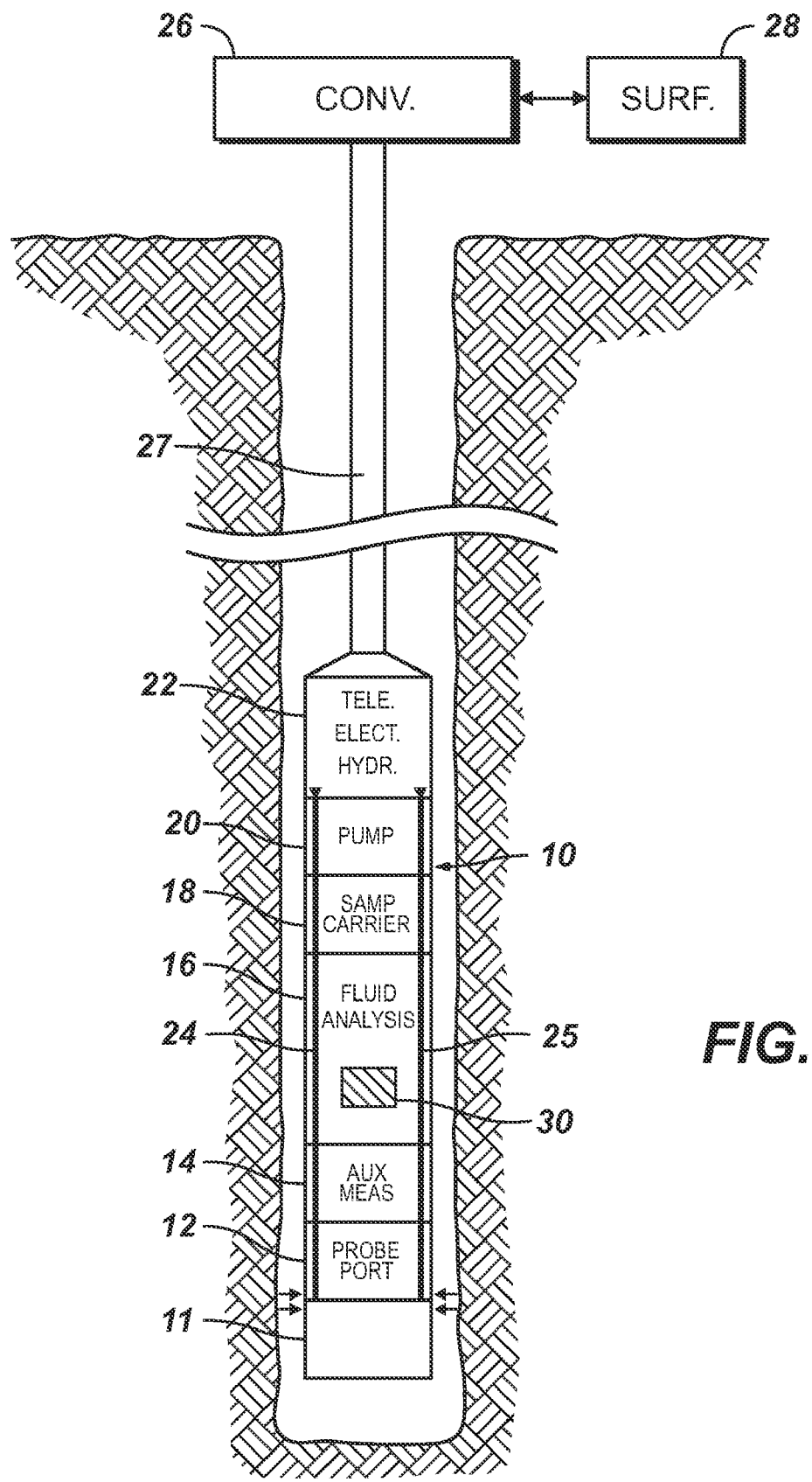
FIG. 1 illustrates a downhole tool having a measurement device for fluid analysis.

A downhole tool 10 in FIG. 1 has a measurement device 30 for in-situ sampling and analysis of fluids in a wellbore. A conveyance apparatus 26 at the surface deploys the tool 10 downhole using a tubular, a cable, a wireline, or similar component 27. As shown in FIG. 1, the tool 10 can be a formation tester such as disclosed in U.S. Pat. Pub. No. 2008/0173083, filed 24 Jan. 2007, which is incorporated herein by reference. However, the measurement device 30 can be deployed in any suitable tool used for wireline formation testing, production logging, Logging While Drilling/Measurement While Drilling (LWD/MWD), or other operations.

1. Downhole Tool

As shown in FIG. 1, the formation tester tool 10 has dual fluid flow lines 24/25 that extend through sections of the tool 10 and that are functionally configurable. However, other types of formation tester tools could also be used, such as those having a single flow line. In operation, a probe 12 having an intake port draws fluid into the tool 10. To isolate the formation fluid samples from contaminates in the annulus, the tool 10 can use isolation elements, such as packers 11 or other devices, to isolate a region of the formation.

A pump 20 then pumps collected fluid from the probe 12 into the tool 10 via the flow lines 24/25. The fluid, which can contain hydrocarbon components (solid, liquid, and/or gas) as well as drilling mud filtrate or other contaminants, flows through the tool 10, and various instruments and sensors in the tool 10 analyze the fluid. For example, a measurement section 14 can have sensors that measure various physical parameters (i.e., pressure, temperature, etc.) of the fluid, and the measurement device 30 in the fluid analysis section 16 can determine physical and chemical properties of oil, water, and gas constituents of the fluid downhole. Eventually, fluid directed via the flow lines 24/25 can either be purged to the annulus or can be directed to the sample carrier 18 where the samples can be retained for additional analysis at the surface.

Additional components 22 of the tool 10 can hydraulically operate valves and other elements within the tool 10, can provide control and power to various electronics, and can communicate data via wireline or fluid telemetry to the surface. Uphole, surface equipment 28 can have a surface telemetry unit (not shown) to communicate with the downhole tool's telemetry components. The surface equipment 28 can also have a surface processor (not shown) that performs additional processing of the data measured by the tool 10.

2. Measurement Device for Downhole Fluid Analysis

As noted above, the fluid analysis section 16 uses the measurement device 30 for downhole fluid analysis. Depending on the configuration and types of sources and detectors used and their orientation relative to a sample, the measurement device 30 can operate as a photometric analyzer, reflectometer, spectroscope, spectrophotometer, spectrometer, or the like. For example, the measurement device 30 can operate as a multi-channel photometric analyzer in which discrete wavelengths are interrogated over a given measurement range. In common usage, such a multi-channel photometric analyzer can be referred to as a spectrometer. Thus, the measurement device 30 can use various spectral channels to perform spectroscopic analysis of downhole fluid passing relative to it as the fluid is pumped through the tool 10 (FIG. 1). As such, the spectroscopic analysis discussed herein can include, but may not be limited to, analysis of transmission, absorbance, or both, and can apply chemometrics, derivative spectroscopy, and other techniques known in the art. Details of how a spectroscope can be implemented in a downhole tool are disclosed in U.S. Pat. No. 7,508,506, which is incorporated herein by reference.

Figure 2A:
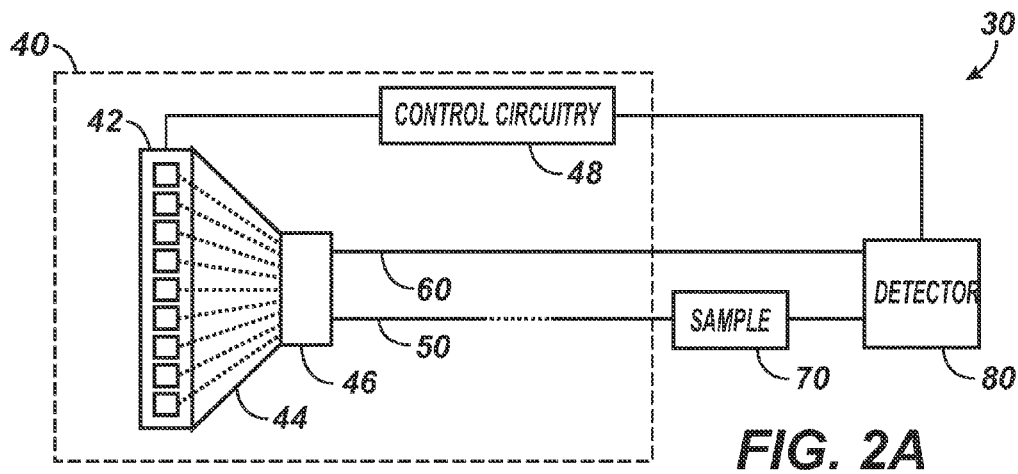
FIG. 2A schematically illustrates a measurement device for fluid analysis having a multi-channel source assembly, reference and measurement channels, a sample unit, control circuitry, and a detector unit.

As schematically shown in FIG. 2A, the measurement device 30 has a multi-channel source assembly 40, a sample unit 70, and a detector unit 80. The source assembly 40 has a plurality of sources 42, a coupler 44, a router 46, and control circuitry 48. When operated, the source assembly 40 generates optical signals with the sources 42, and the coupler 44 combines the generated signals from the sources 42 and couples the combined signal to the router 46. In turn, the router 46 routes the combined signal into a reference channel 60 and into a measurement channel 50 for interrogating a sample.

The downhole source assembly 40 preferably meets particular characteristics. Preferably, the source assembly 40 offers a broadband source of optical signals (EM radiation), but contains a number of independently operable channels (i.e., wavelength regions) that are spectrally aligned to cover a broad spectral range. Therefore, the individual sources 42 generating the optical signals preferably have a discrete wavelength or a distribution of wavelengths across a spectrum of wavelengths, and the sources 42 preferably provide unique optical channels (i.e., wavelength regions) of interest that are amenable to various applications and wavelengths of interest in a downhole environment.

In general, the combination of sources 42 can provide a continuous spectral distribution over a broad spectral range. Alternatively, the sources 42 can cover a broad spectral range having a non-continuous spectral distribution of two or more spectrally continuous regions interposed by at least one spectrally dark region. As discussed below and depending on the implementation, each source 42 is preferably capable of independent modulation at a unique or independent frequency, which enables synchronous detection. In addition, one or more of the sources 42 may be spectrally filtered and spatially shaped using a series of optical elements. Finally, the source assembly 40 preferably enables continuous signal scaling using in-situ reference and dark correction and is preferably energy efficient and long lived. In addition, the source assembly 40 preferably enables dynamic scaling by using its integrated reference channel and dynamic dark correction and using its ability to turn all sources 42 off or block all output in the measurement and reference channels on command. Finally, the source assembly 40 is preferably energy efficient and long lived.

To help meet the above characteristics, the sources 42 in the assembly 40 preferably include multi-channel solid state sources, including but not limited to light emitting diodes (LED), super-luminescent light emitting diodes (SLED), and laser diodes (LD), where each of the individual sources 42 are coupled using a fiber bundle, a fiber coupler such as a star coupler, a bulk spectral coupler, or some other coupler 44 as disclosed herein.

Figure 2B:
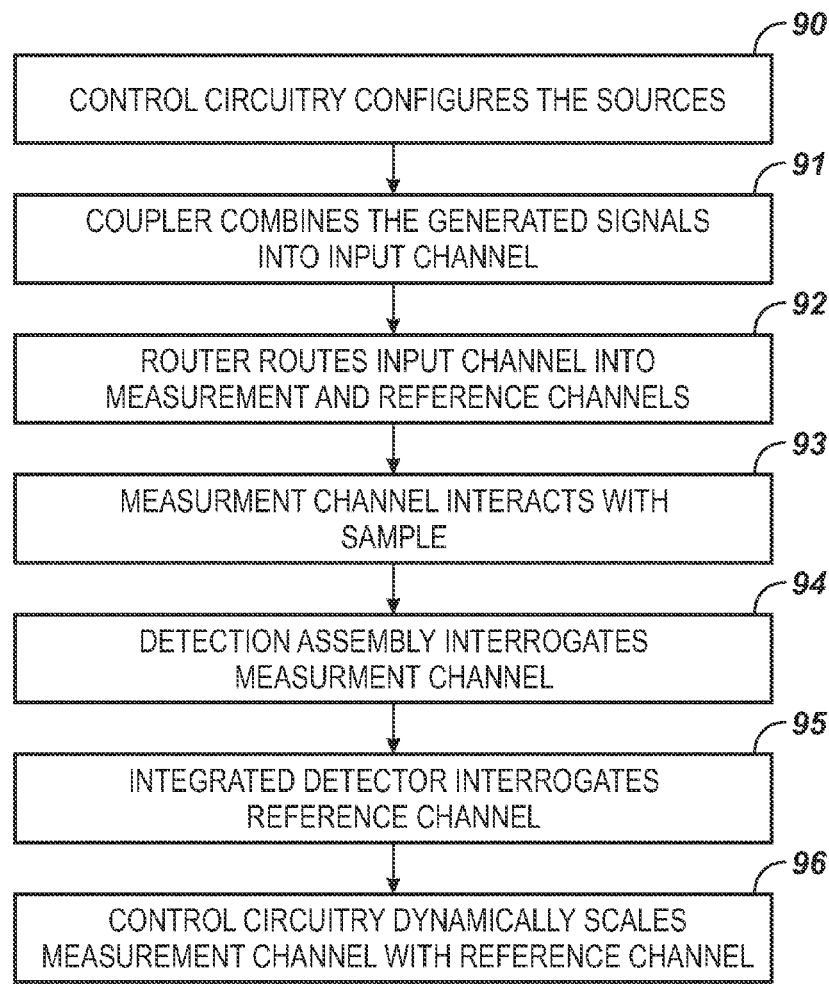
FIG. 2B shows the general operation of the measurement device shown in FIG. 2A

More detailed operation of the measurement device 30 is discussed concurrently with reference to FIG. 2B. The control circuitry 48 modulates the assembly's individual sources 42 at unique or independent frequencies and encodes the generated signals so that Conventional Raster Scanning (CRS), Fourier Transform (FT), or other methods known to those skilled in the art can be used for spectroscopic analysis (Block 90). The coupler 44 optically couples to the generated signals of each of the sources 42 and combines the generated signals into an input channel (Block 91). Optically coupled to this input channel, the router 46 routes the input channel into a measurement channel 50 and a reference channel 60 (Block 92). Throughout this disclosure, these channels 50/60 or light paths are referred to as a "measurement channel" and a "reference channel" to indicate that the measurement channel 50 interrogates a sample with EM radiation while the reference channel 60 is used for continuous referencing. Although one measurement channel 50 is shown along with one reference channel 60, it will be appreciated that multiple measurements channels 50 can be provided for the same reference channel 60. Therefore, the device 30 can have several measurement channels 50 along with sample assemblies 70 and detector units 80 for separate analysis.

For the measurement channel 50, the encoded signals interact with a sample fluid via the sample unit 70 (Block 93). For its part, the sample unit 70 can use different designs, including, but not limited to, a sample cell, a reflectance accessory, a transmittance accessory, a fluorescence accessory, an Attenuated Total Reflectance (ATR) accessory, an extractive flow cell, or any other sampling or monitoring device known to those skilled in the art. After interaction with the sample, the detector unit 80 detects the measurement channel 50 for analysis (Block 94). Detectors in the unit 80 can cover the required spectral bandwidth provided and can use any of the various available detector materials (i.e., Si, InGaAs, PbS, PbSe, MCT, etc.) and any of the various available configurations (i.e. photodiodes (PD), avalanche photodiodes (APD), photomultiplier tubes (PMT), Multi-Channel Plates (MCP), etc.). Details of the detector unit 80 are disclosed in co-pending application Ser. No. 12/613,808 entitled "Multi-Channel Detector Assembly for Downhole Spectroscopy," which has been incorporated herein in its entirety.

Concurrent with the interrogation of the measurement channel 50, the reference channel 60 is also interrogated (Block 95). The control circuitry 48 receives detected signals from the detector unit 80, containing both the measurement and reference detectors. Then, the control circuitry 48 correlates the received signals and continuously scales the measurement channel 50's signal by the reference channel 60's signal to account for downhole environmental conditions, drift, or the like (Block 96). Once the received signals are scaled and decoded, the resulting spectral data can be used to determine chemical and/or physical properties of the sample fluid. This can be performed by the control circuitry 48 or by some other controller. Ultimately, as referenced above, the measurement device 30 of FIG. 1 can transmit spectral data to a processing system (not shown) located on the tool 10 or at the surface equipment 28.

B. Downhole Multi-Spectral Source Assembly

Figure 3A:
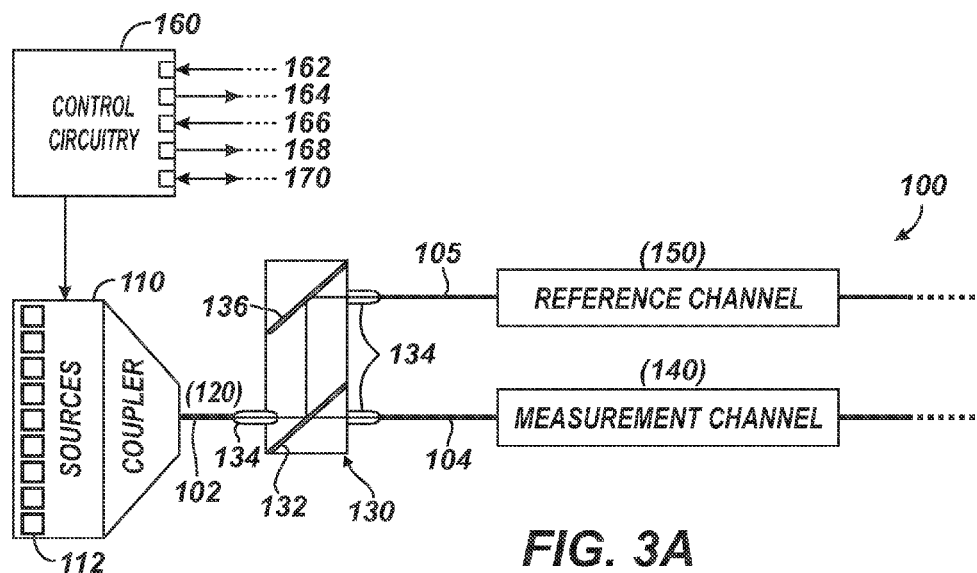
FIG. 3A illustrates a first arrangement of a multi-channel source assembly having a multiple spectral sources and having a router assembly with a splitter and reflector.
Figure 3B:
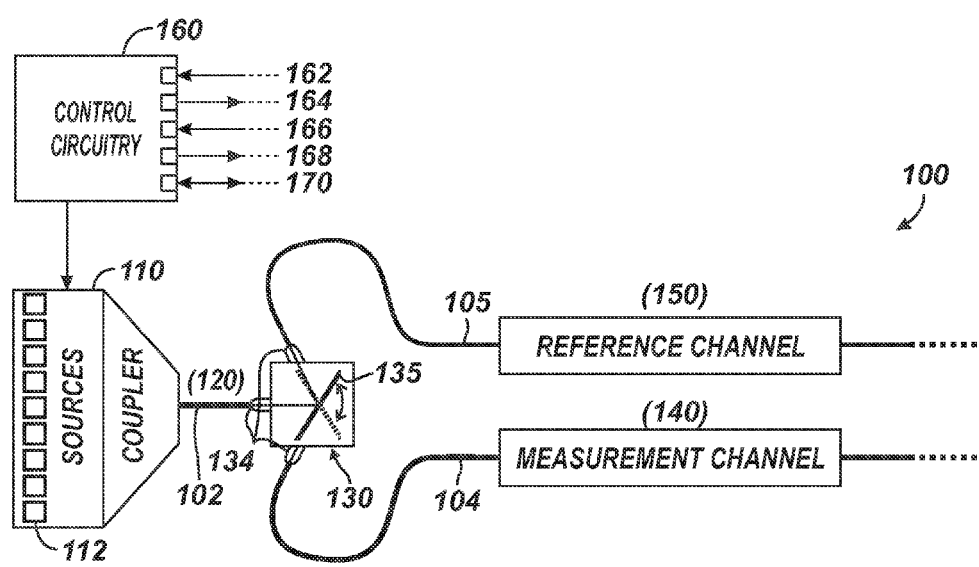
FIG. 3B illustrates a second arrangement of a multi-channel source assembly having multiple spectral sources and having an adaptive optical element.

With an understanding of the measurement device 30 and the downhole tool 10 in which it can be deployed, discussion now turns to FIGS. 3A-3B showing different arrangements of a multi-channel source assembly 100 for downhole spectroscopy according to certain teachings of the present disclosure.

1. First Arrangement Having Router with Splitter and Reflector

In a first arrangement shown in FIG. 3A, the multi-channel source assembly 100 has a source-coupler unit 110, a router assembly 130, and control circuitry 160. As discussed briefly above and in more detail later, the source-coupler unit 110 has a plurality of sources 112. The control circuitry 160 can electrically modulates each individual source 112 at a unique or independent frequency, and the unit 110 optically couples the generated signals of each individual source 112 to an input channel 120, which may be carried by an individual fiber, a fiber bundle, or other device 102 as disclosed herein.

At the router assembly 130, an optic 134, such as a collimator, collimates the input channel 120, and a fractional beam splitter 132 then creates fractional beam intensity along separate optical paths to produce two separate channels—a measurement channel 140 and a reference channel 150. To achieve the highest possible signal-to-noise ratio in the measurement channel 140, only a small portion (i.e., 5-10%) of the input channel 120 is routed into the reference channel 150. The remaining percentage is routed into the measurement channel 140. Overall, the use of a reference channel 150 improves the accuracy and precision of the resulting measurement.

As shown, the router 130 creates a first optical path constituting a first fraction or majority of the input channel 120. This first optical path passes through an optic 134 to an optical path 104 for the measurement channel 140. As shown, this path 104 can use a fiber or can pass through free space. The router 130 also creates a second optical path constituting a second fraction or minority of the input channel 120. In one implementation, the measurement channel 140 constitutes 90% of the input channel 120, while the reference channel 150 constitutes 10% of the input channel 120, although other percentages could be used in other implementations.

The second optical path from the splitter 132 passes to a reflector 136, which can be a mirror, a prism, or other comparable device. The reflector 136 directs the reference channel 150 through another optic 134 and into an optical path 105 for the reference channel 150. Again, this path 105 can use a fiber or can pass through free space. In this way, the reflector 136 enables the optical paths 104/105 carrying the two channels 140/150 to be positioned adjacent and parallel to one another to conserve space in the source assembly 100 used downhole.

After splitting, the measurement channel 140 can be used to analyze fluid using sample and detector units (not shown), for example, or for other purposes. For its part, the reference channel 150 can be used to provide optical feedback from the detection unit (not shown) to the control circuitry 160 for controlling the sources 112, to dynamically scale the optical signal of the measurement channel 140, and to perform other functions as discussed in more detail below.

As shown in FIGS. 3A and 3B, the control circuitry 160 has a number of inputs and outputs that can be used for various purposes discussed later. (See e.g., FIG. 16). Briefly, the control circuitry 160 has a digital/trigger input 162, digital/trigger output 164, and a communications interface 170 that can be used for external control of the control circuitry 160. Also, an analog input 166 can be used for an automated control scheme and can receive analog measurement signals from separate detectors. Finally, either the analog output 168 or communications interface 170 can be used for messaging, such as sending status messages concerning the health of the source assembly 100. For example, the control circuitry 160 can use the inputs and outputs to interact with external control circuitry (not shown) of a detection system and to dynamically adjust the source assembly's operation based on that interaction.

2. Second Arrangement Having Router with Scanning Optic

In a second arrangement shown in FIG. 3B, the source assembly 100 again has source-coupler unit 110, router assembly 130, and control circuitry 160. Generating the input channel 120 can follow the same course as discussed previously. In contrast to the previous arrangement, the router assembly 130 uses an adaptive optical element or scanning optic 135 (as opposed to the fractional beam splitter 132 as in FIG. 3A) to route the input channel 120 into separate channels 140/150. The scanning optic 135 can be a scanning mirror, Micro-Electro-Mechanical System (MEMS) scanning mirror. Details of using a scanning optic are disclosed in U.S. Pat. No. 7,508,506, which has been incorporated herein by reference in its entirety.

In use, an optical assembly 134 at the router assembly 130 collimates the input channel 120 generated by the source-coupler unit 110. Then, the scanning optic 135 routes the input channel 120 by serially directing all of the input channel 120 at two optical assemblies 134 relative to the scanning optic 135. Furthermore, the input optical assemblies 134 can be used to improve the beam shape, dispersion, or intensity using various available optics not shown for simplicity. In addition, the scanning optic 135's orientation is controlled via a controller—either independent from or integrated into the control circuitry 160.

In one orientation, for example, the scanning optic 135 directs all of the input channel 120 to an optic 134 and along light path 104 for the measurement channel 140, which can interact with sample and detector units (not shown). Once oscillated or rotated, the scanning optic 135 then directs all of the input channel 120 to an optic 134 and along light path 105 for the reference channel 150, which can be interrogated by a detector unit (not shown). As should be apparent, because the switch between the two channels 140/150 having the spectrum of interest can occur relatively quickly and repeatedly, the reference channel 150 can be used to normalize the output of the measurement channel 140 to provide for a dynamically scaled reading. As implemented, the scanning optic 135 asynchronously images the total intensity of the input channel 120 to the reference and measurement channels 140/150, as opposed to fractionally splitting the intensity between measurement and reference channels 150/140 in FIG. 3A. Consequently, the scanning optic 135 can provide an enhanced signal-to-noise ratio, especially if it is run at a substantially lower frequency relative to the modulation of the individual sources 112. In addition, multiple measurements channels (not shown) could be utilized with this implementation.

In FIGS. 3A-3B, two arrangements for the source assembly 100 have been shown. It will be appreciated with the benefit of the present disclosure that other arrangements are possible and that components from one of the disclosed arrangements can be exchanged or combined with those of another arrangement disclosed herein.

C. Housing Arrangements for Multi-Channel Source Assembly

Because the source assembly 100 is used downhole, housing its components can be constrained by the available tool space and the downhole environmental specifications. Ideally, components of the source assembly 100 have a housing that is amenable to downhole deployment and that can fit into the tight downhole space required in a downhole tool. Therefore, the source assembly 100 is preferably constructed as a discrete modular unit that can be incorporated or connected to other modular units for sampling and detection in a downhole tool.

Figure 4A:
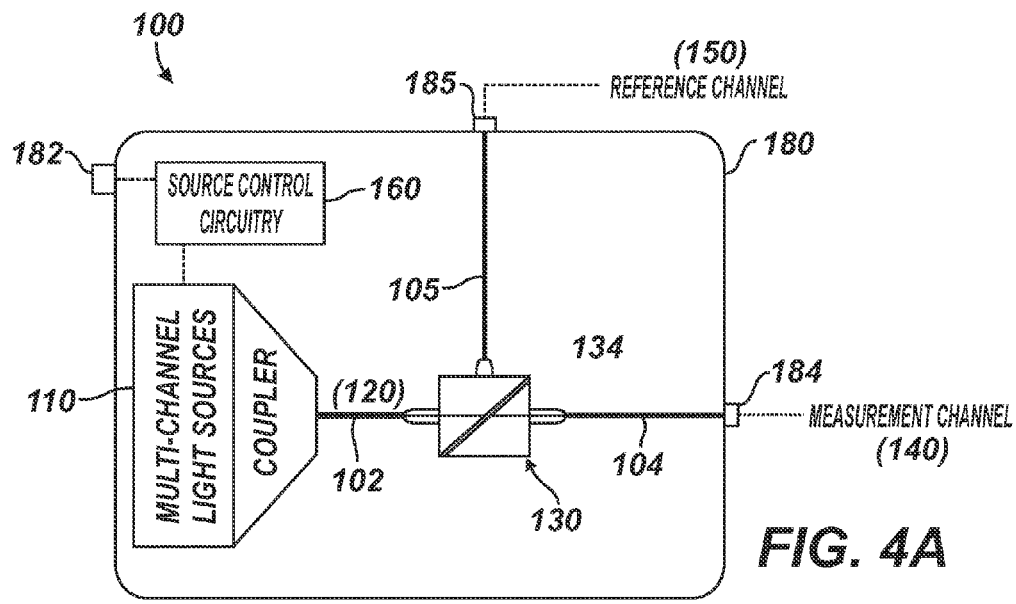
FIGS. 4A-4B illustrate housing arrangements for the disclosed multi-channel source assembly.
Figure 4B:
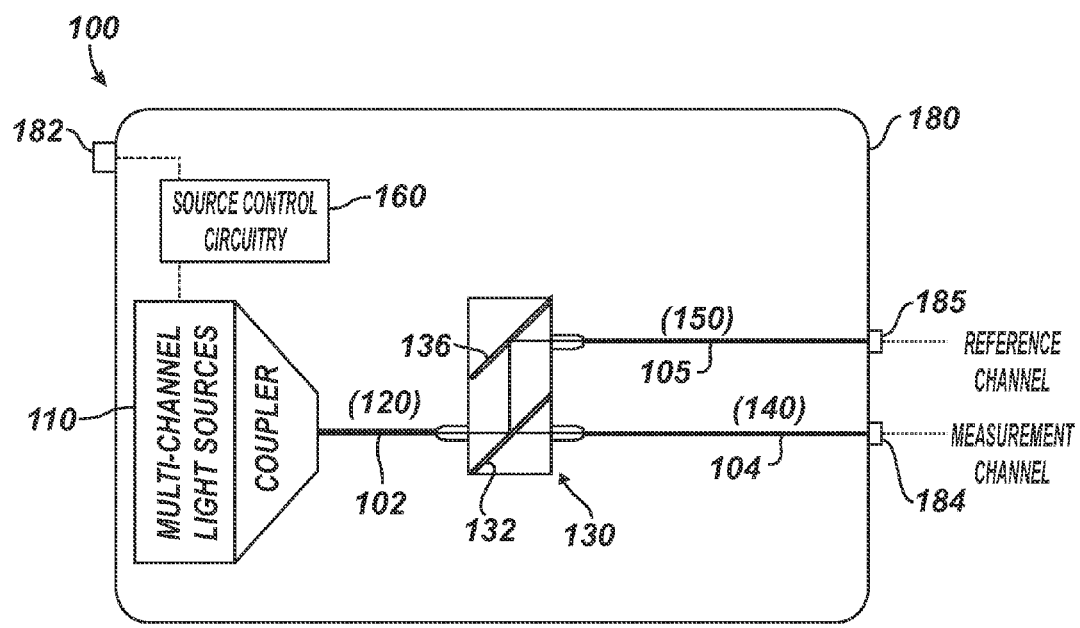

FIGS. 4A-4B illustrate housing arrangements for the source assembly 100 disclosed herein. In one example, the source assembly 100 in FIG. 4A has a housing 180 that contains a source-coupler unit 110, a router assembly 130, and control circuitry 160 similar to those discussed previously. Externally, the housing 180 has at least one electrical connector 182 for coupling the internal components to power, environmental sensors (not shown), communications, and external control elements (not shown). In addition, the housing 180 has at least two optical connectors 184/185 that couple the housing 180 to other units. For example, one optical connector 184 can carry the measurement channel 140 to the sample unit and the detection unit (not shown), and the other optical connector 185 can carry the reference channel 150 to the detector unit (not shown).

Figure 14A:
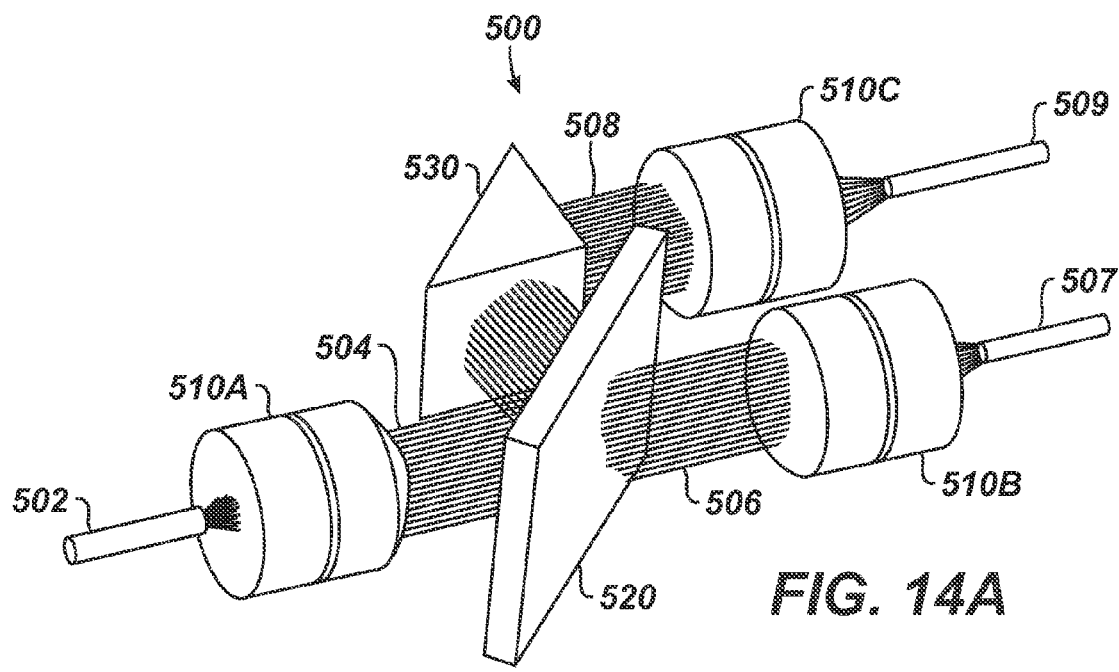
FIGS. 14A-14B illustrate a routing assembly having a splitter/reflector.
Figure 14B:
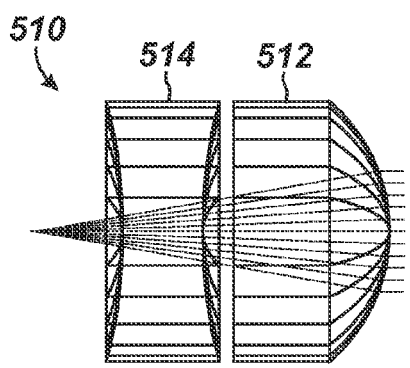

In another example, the source assembly 100 in FIG. 4B has a housing 180 again containing a source-coupler unit 110 and a router assembly 130. Externally, the housing 180 has at least one electrical connector 182 for coupling the internal components to power, environmental sensors (not shown), and external control elements (not shown) and has one optical connector 184 that couples the housing 180 to the sample unit and the detection unit (not shown) for the measurement channel 140. For compactness, optical fibers or optical light paths 104/105 for the channels 140/150 are arranged parallel to one another in the housing 180. To do this, the router assembly 130 has a splitter 132 and a reflector 136 that splits the input channel 120 into the measurement channel 140 for fiber or optical light path 104 and into the reference channel 150 for fiber or optical light path 105. (Details of such a router having combined splitter and reflector are illustrated in FIGS. 14A-14B).

To remain small and rugged, the housings 180 and components discussed above are preferably kept within various size constraints. To withstand use downhole, the housings 180 for the assembly 100 also preferably meet shock and vibration requirements for the downhole environment.

Although the housing arrangements in FIGS. 4A-4B have been described using only some of the components from the arrangements in FIGS. 3A-3B, it will be appreciated that additional housing arrangements are possible using other components of the source assembly 100 disclosed herein.

D. Multi-Source Coupler Assemblies

As discussed previously in FIGS. 3A-3B, the source assembly 100 uses a source-coupler unit 110 that generates optical signals with a plurality of individual sources 112 and combines the optical signals together into an input channel 120. FIGS. 5A through 12B below disclose a number of combinations of sources and couplers that can be used for the source assembly 100.

1. Individual Sources and Couplers

Figure 5A:
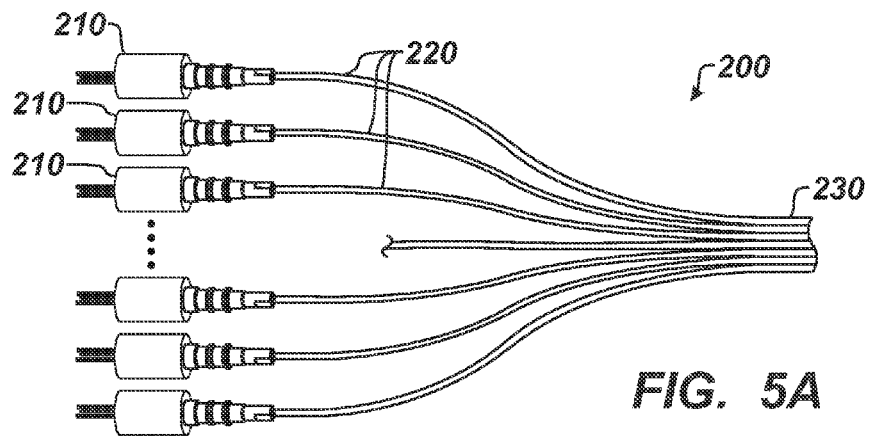
FIG. 5A illustrates a beam coupling assembly having individual sources and fibers.

In FIG. 5A, a source-coupler unit 200 has individual sources 210 and optical couplers 220. The individual sources 210, which can be electronic sources such as LEDs or the like, can be spectrally convolved or individually selected so their generated light can be used for spectroscopy or other analysis. For example, the control circuitry (160; FIGS. 3A-3B) can illuminate the sources 210 using raster scanning, frequency modulation, or other techniques discussed herein.

Generated signals from each source 210 are optically coupled into its individual optical coupler 220, which each have one end optically coupled to one of the sources 210. As shown, each of these couplers 220 can be an optical fiber, although other individual optical couplers can be used, including optical waveguides, light pipes, mirrored conduits, or the like. Each of these individual fibers 220 then bundle together with one another to form a fiber bundle 230. Eventually, the end of the fiber bundle 230 can optically couple to a router assembly (130; FIGS. 3A-3B) or can be imaged into a single fiber (See FIGS. 7 & 9) for coupling to the router assembly. As an alternative to the use of individual fibers 220, bulk optical or micro optical, free-space types of couplings can be used for the source assembly. Details of one such arrangement are disclosed herein.

Figure 5B:
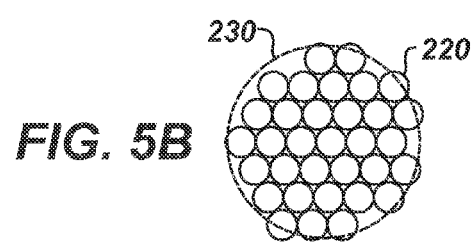
FIG. 5B illustrates an end-view of a fiber bundle for the beam coupling assembly of FIG. 5A.

FIG. 5B illustrates an end-view of the fiber bundle 230 composed of the individual fibers 220. As shown, the bundle 230 is a close-packed arrangement of the fibers 220. Each fiber 220 can be a stripped 100-μm core/110-μm clad fiber having a numerical aperture (NA) of 0.22. In this way, the bundle 230 of fibers 220 can have an approximate diameter of 700-microns and can behave like a 700-micron diameter point source for coupling to the router (130; FIGS. 3A-3B) or to a single fiber (See FIGS. 7 & 9).

Figure 6A:
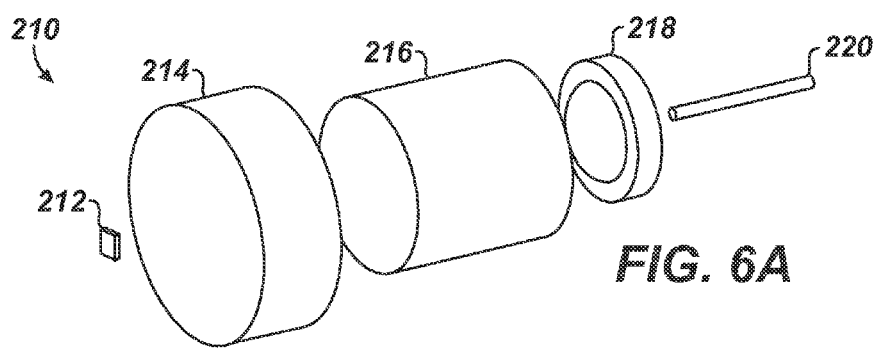
FIGS. 6A-6B illustrate a fiber coupling between an individual source and an optical channel.
Figure 6B:
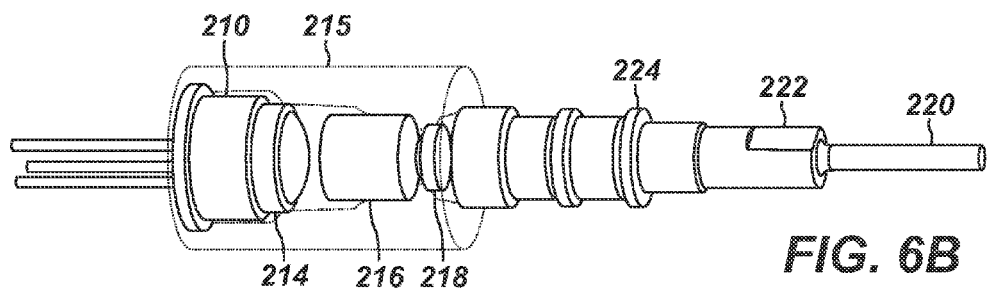

Various optical elements may be used to image the generated light from the sources 210 to its corresponding fiber or light path 220, and some of the sources 210 may or may not require an optical filter. FIGS. 6A-6B show a representative optical coupling between a source 210 to an optical fiber or light path 220; however, those skilled in the art will recognize that alternative coupling methods could be used for this purpose.

As shown in FIG. 6A, generated light from the source 210 (shown having an LED die 212) is individually collimated and focused onto the fiber 220's end face. As shown, a collimating lens 214, a filter 216, and a coupling lens 218 are positioned between the source's die 212 and the optical fiber 220. The lenses 214 and 218 have a region between them through which collimated light can pass through the filter 216. Positioned in this region, the filter 216 may require a relatively small range of angles in order to function correctly. If the LED source 210 does not require filtering, a single lens may instead be used between the LED source 210 and the fiber 220.

As shown in FIG. 6B, the source 210 can have a TO-46 header, and a collar 215 can house the collimating lens 214, filter 216, and coupling lens 218 in fixed distances relative to the source 210's header. A sleeve 224 and a fiber ferrule 222 connect from the collar 215 to the optical fiber 220, which can be either a multimode or single mode fiber optic cable. In one arrangement, the multimode fiber optic cable employed has a 100-micron core diameter.

The filter 216 is a wavelength selection filter (i.e., a bandpass filter). Preferably, the filter 216 is a hard-coated metal oxide bandpass filter compatible with downhole conditions. When used, the optical filter 216 reduces the adverse effects caused by the source's spectral characteristics (i.e., center wavelength and spectral bandpass) changing with temperature downhole. Although the optical filter 216 still changes center wavelength and bandpass, it may do so to a significantly lesser extent than the source 210 itself. Therefore, in some implementations, use of the filter 216 may be preferred.

Figure 7:
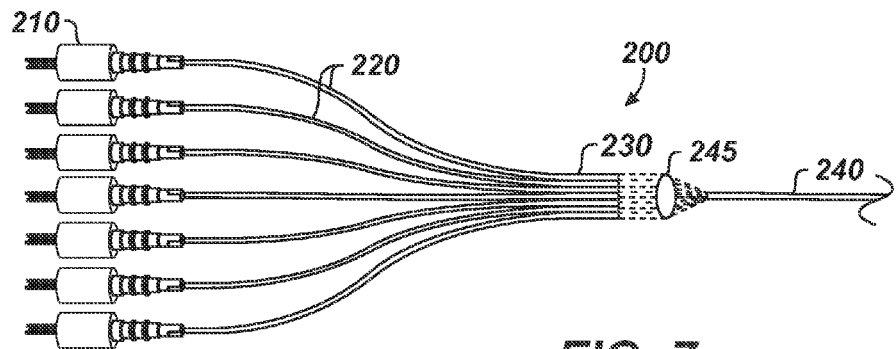
FIG. 7 illustrates how the beam coupling assembly of FIG. 5A-5B can be imaged into a single optical channel.

As shown in FIG. 7 and noted previously, individual sources 210 separately couple to optical fibers 220 that are formed into a fiber bundle 230 as with FIGS. 5A-5B. As shown here, this bundle 230 optically couples to an optic lens 245 that images the generated signals into an input fiber 240 that can carry the signal to a router (130; FIGS. 3A-3B), as discussed previously.

Figure 8:
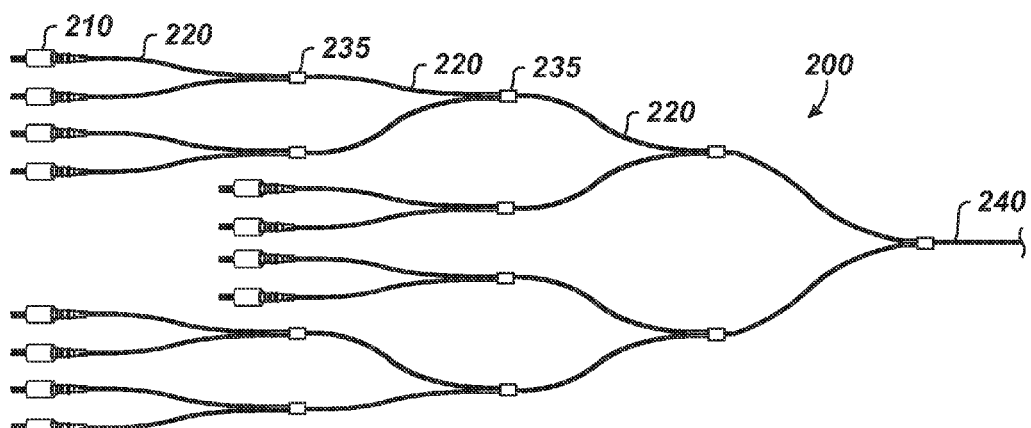
FIG. 8 illustrates another beam coupling assembly having a tree topology.

In an alternative shown in FIG. 8, individual sources 210 are each imaged into its own optical fiber 220, which can be done in a similar fashion described previously. Each optical fiber 220 is then fused with another source's fiber 220 using a coupling member 235 that combines the input signal from fused fibers 220 into an output signal for an output fiber 220. Then, the multiple sources 210 and fibers 220 are combined in a tree or star topology 200, and the generated signals are subsequently combined into a common optical beam carried by an input fiber 240 to a router (130; FIGS. 3A-3B), as discussed previously.

2. Individual Sources and Segmented Mirror

Figure 9:
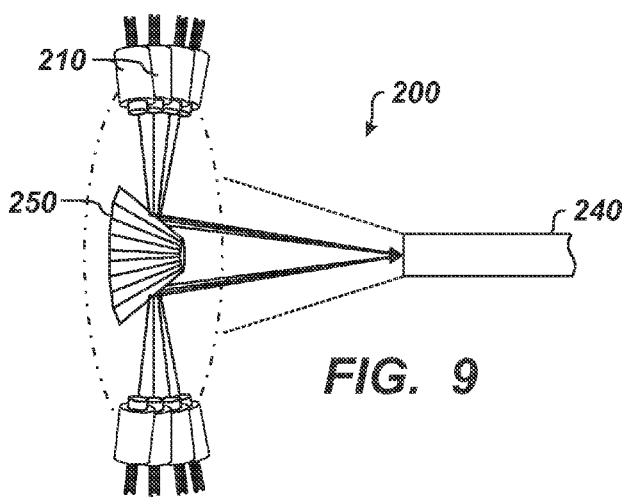
FIG. 9 illustrates another beam coupling assembly having a segmented mirror.

In FIG. 9, another source-coupler unit 220 for the disclosed source assembly has a segmented mirror 250. In this arrangement, the individual sources 210 are arranged in a circular or ring configuration—only a portion of which is shown. The segmented mirror 250 surrounded by these sources 210 images their light to the end of an input fiber 240, which can be a single, large-core fiber optic cable or a fiber bundle, as well as a free space optical channel. In turn, the input fiber 240 can convey the input channel to a router (130; FIGS. 3A-3B), as discussed previously.

3. Individual Sources and Bulk Optical Combiners

In FIGS. 10A-10B, source-coupler units 200 for the disclosed source assembly have individual sources 210 imaged in a bulk arrangement into an input fiber or light path 240. In FIG. 10A, for example, the unit 200 has a series of low pass filters 260 that combine generated signals from the individual sources 210 into a common optical beam. At the end of the filters 260, an optic lens 262 images the common beam into the input fiber or light path 240. As shown, bandpass filters 216 may be used between the sources 210 and the series of low pass filters 260. Because low pass filters 260 are used, the various source/filter combinations increase in wavelength ($\lambda_0$-$\lambda_7$) as they are positioned closer to the input fiber 240 into which the common beam is imaged.

The sources 210 and filters 216/260 can be arranged at acute angles (as in FIG. 10A) or arranged perpendicularly (as in FIG. 10B). In addition, the unit 200 in FIG. 10B has a series of high pass filters 264 (as opposed to low pass filters) that combine light from the individual sources 210 into the common optical beam. For this arrangement, the various source/filter combinations decrease in wavelength ($\lambda_7$-$\lambda_0$) as they are positioned closer to the input fiber 240 into which the common beam is imaged.

In addition to the above arrangements, FIGS. 11A-11B show additional bulk arrangements of individual sources 210 and filters 266. Here, the sources 210 are arranged in non-linear clusters and use filters 266 to direct and combine the wavelengths of interest from the sources 210. Ultimately, the optical signals are directed to a lens 262 that images the combined signal into the input fiber 240. These configurations minimize the distance between the sources 210 and the input fiber or light path 240, thereby minimizing optical losses.

4. Bulk Optical Couplers Having Microbenches

Additional bulk optical couplers used for the source assembly 100 can use microbenches. As shown in a source-coupler unit 300 in FIG. 12A, various sources 310 position in patterns formed in the microbench 302. These patterns can be etched or micromached in the bench 302 using known techniques. A series of mirrors 312 are disposed in slots in the bench 302. Generated signals from the sources 310 are imaged onto the mirrors 312 that in turn reflect the signals to an optic lens 314. In turn, the lens 314 images the combined beam into a fiber, a fiber bundle, or light path 330 that carries the input channel to a router assembly (130; FIGS. 3A-3B), as discussed previously.

Figure 12A:
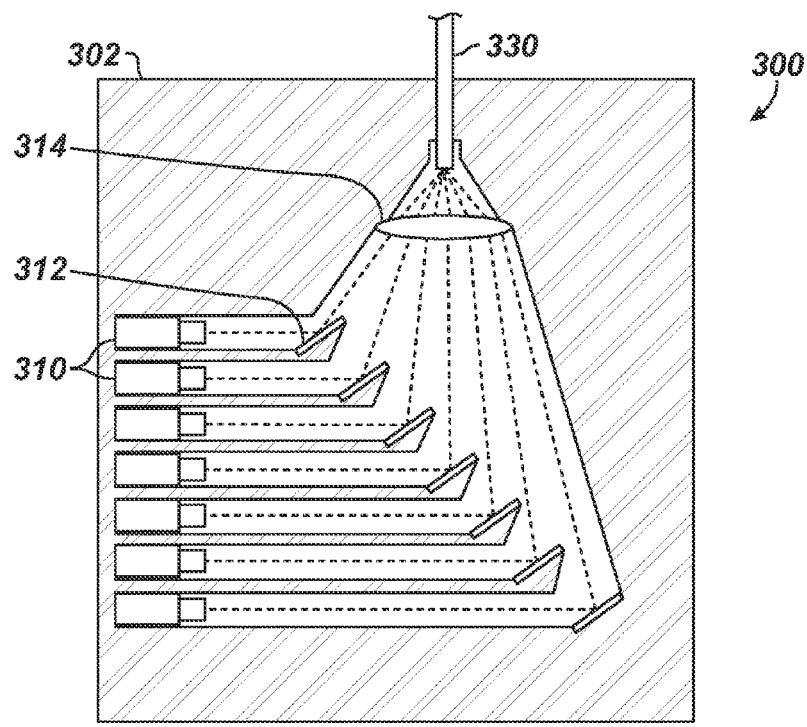
FIGS. 12A-12B illustrate bulk coupling assemblies utilizing optical microbenches.
Figure 12B:
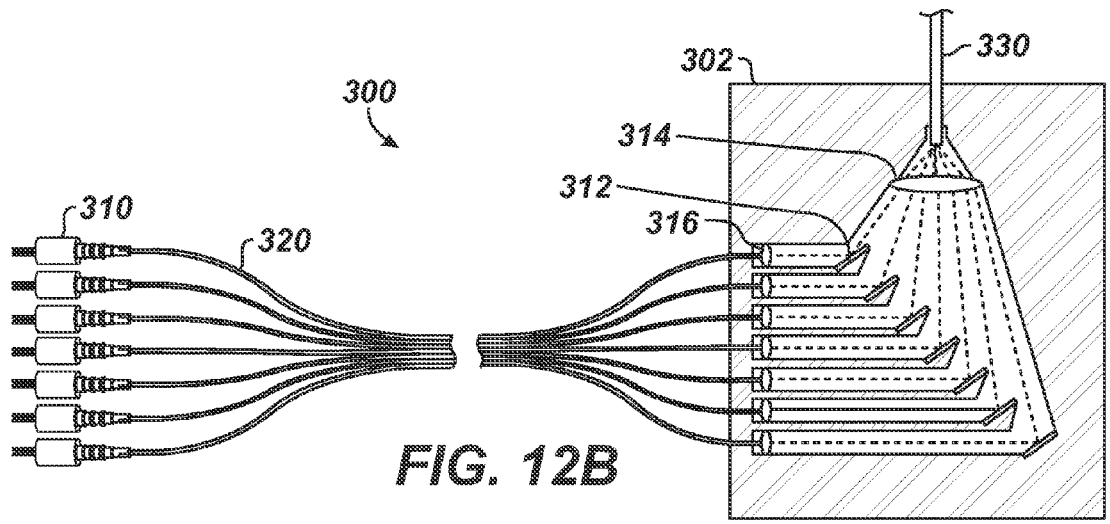

A similar arrangement in FIG. 12B has input fibers 320 that carry generated signals from individual sources 310 to optic lenses 316. In turn, the lenses 316 image the signals onto the mirrors 312, and an optic lens 314 receives signals from the mirrors 312 and images the combined beam into the fiber or bundle 330. As will be appreciated, the microbench 302 allows the elements to be precisely aligned during manufacture and closely housed, which is advantageous for downhole use.

5. Individual Sources and Grating Couplers

In FIG. 13A, a source-coupler unit 400 for the disclosed source assembly uses an array 420 of individual sources 410, a grating 430, and a controller 460, which can be part of the source assembly's control circuitry (160; FIGS. 2A-2B). As shown, the individual sources 410, which can be LEDs or the like, are spatially configured on the array 420. The sources 410 generate optical signals in different spectral bands and can be activated in a number of patterns to encode the generated signals. In particular, the sources 410 can be arranged in off-set rows of a number of columns with the wavelength assigned for a particular source 410 depending on its location in the array 420. For example, sources 410 may be arranged with increasing wavelengths along the axis of the array 420.

Controller 460 coupled to the array 420 can have a microprocessor 462, a pattern generator 464, and an array driver 466 to encode the illuminations of the sources 410. During use, the controller 460 selectively illuminates the sources 410 to encode their generated optical signals in a desired pattern. Depending on the implementation, the illumination pattern may require that either a Hadamard transform, a Fourier transform, or other method be used to deconvolve the optical signals received at the detection assembly (not shown).

The reflective grating 430, which can be concave with its reflective focal surface incorporating fine rulings, reflects and diffracts the generated signals from the sources 410 and directs the reflected beam 431 to a lens 435. In turn, the lens 435 images the beam 431 into a common input beam (120) that is directed to a router 130 similar to that discussed previously. The splitter 132 in the router 130 then partitions the input beam (120) into the measurement channel (140) and the reference channel (150) for use according to the purposes disclosed herein.

As an alternative to the router assembly 130, the source-coupler unit 400 can instead use a combiner 440 shown in FIG. 13B to produce the measurement and reference channels (140/150) from the grating's reflected beam 431. The combiner 440 has a slit 442 disposed relative to two optical fibers 444/445. The reflected beam 431 from the grating (430) is directed to the combiner 440, where the slit 442 images the beam 431 to the spatially registered fibers 444/445. The first fiber 444 is for the measurement channel (140), while the second fiber 445 is for the reference channel (150). As shown, the measurement channel's fiber 444 can be larger than the reference channel's fiber 445 so that a higher fraction of the common beam is imaged onto it. However, the spatially registered fibers 444/4445 can be of comparable size depending on the implementation.

In FIG. 13C, the source-coupler unit 400 again uses the array 420 of individual sources 410, the reflective grating 430, and the controller 460 operating as described above. However, rather than using a router 130 (FIG. 13A) or combiner 440 (FIG. 13B), the reflective grating 430 reflects a first order reflected beam 432 to a first lens 433 and reflects a second order reflected beam 436 to a second lens 437. The first lens 433 images the first order beam 432, which is stronger, into the measurement channel (140), while the second lens 437 images the second order beam 436 into the reference channel (150). By using the first and second order reflections from the grating 430, the unit 400 can avoid using a beam splitter or other router devices, which can improve the spectral efficiency of the unit 400.

As an alternative to the reflective grating 430, the unit 400 in FIG. 13D uses a transmissive grating 450. Here, the sources 410 are arranged so that a common input beam (120) can be formed using the transmissive grating 450 and a lens 455. The array 420 of individual sources 410 and the controller 460 can operate the same as described previously, and the input beam (120) can be carried to a router (not shown). In general, the substrate of the gratings 430/450 can be composed of metal, glass, silicon carbide, ceramic, quartz, sapphire, or the like. The materials specified are amenable to high temperature applications.

E. Router Having Splitter and Reflector

In FIG. 14A, a router 500 (discussed briefly in FIG. 4B) for the disclosed source assembly has an integrated splitter 520 and reflector 530 to route an input channel into a reference channel and a measurement channel. In FIG. 14A, internal components of the router 500 are shown without the surrounding housing components and other necessary features known and used in the art to contain these components. The router 500 has an input collimation optic 510A that receives the input light signal from an input fiber or bundle 502 that carries the common optical beam from the multiple sources. The collimated input signal 504 from the optic 510A passes to a splitter 520 that splits the input signal 504 into a measurement signal 506 and a reference signal 508. The measurement signal 506 passing from the splitter 520 reaches an optical element 510C that condenses the light and images it into a measurement fiber 507. The reference signal 508 passing orthogonal to the measurement signal 506 reaches the reflectors 530 (i.e., a right angle prism or other mirrored optical element) that directs the reference signal 508 to another optical element 510B. Following collimation by this optic 510B, the reference signal is imaged into the reference fiber 509.

The optical element 510C and input measurement fiber or light path 507 are displaced slightly due to the walk-off induced by the splitter 520. For the current implementation, the region between the collimator optic 510A and condensing optic 510B preferably has a nominal distance such that the transmission performance through the assembly is optimized. The size of the region may differ, however, depending on the wavelengths, size of optical fibers, and other factors.

The pickoff loss in the splitter 520 is preferably minimized so that the potential signal that can reach detectors (not shown) is maximized. For this reason, the splitter 520 is preferably composed of infrared grade fused quartz with a transmission profile that spans the measurement wavelengths of interest and minimizes optical loses. For example, the splitter 520 can be a 1-mm thick fused quartz plate. Other possible materials for the splitter 520 include fused Silica 0 deg., fused Silica 45 deg., sapphire at 45 Deg., or any other optical material known to those skilled in the art. Adjacent the splitter 520, the right angle prism 530 allows both fibers or light paths 507/509 to be parallel for mechanical reasons. Optical element 510B is placed in the same plane as optical element 510C. This is useful for mechanical reasons but may require a different working distance to the fibers or light paths 507/509.

In general, the optics 510A-C as well as other optical elements (e.g., optics 134; FIGS. 3A-3B) disclosed herein can be an achromatic lens, an achromatic lens pair, a plano-convex lens optically coupled to a bi-convex lens, a reflective optical element, a mirror, a holographic optical element, or an adaptive optical element. FIG. 14B shows an arrangement for a collimation optic 510 for use in the router 500 of FIG. 14A as well as other components disclosed herein. The optic 510 is a type of achromatic lens having a plano-convex (PCX) lens 512 and a bi-concave lens 514, which can have a physical separation using a spacer (not shown) or which can be cemented using a suitable optically transmissive cement. The optical cement used must be able to withstand downhole operating temperatures. The material types and forms of the two lenses 512/514 are chosen to have temperature dependent performance characteristics that maximize optical throughput across the required thermal and spectral ranges. Thus, as wavelength varies, the focal length of the bi-concave lens 514 changes more rapidly than that of the plano-convex lens 512. This disparate change in focal length with wavelength serves to reduce the overall dependence of the combined focal length over a range of wavelengths.

F. Measurement Device and Source Arrangement

Figure 15A:
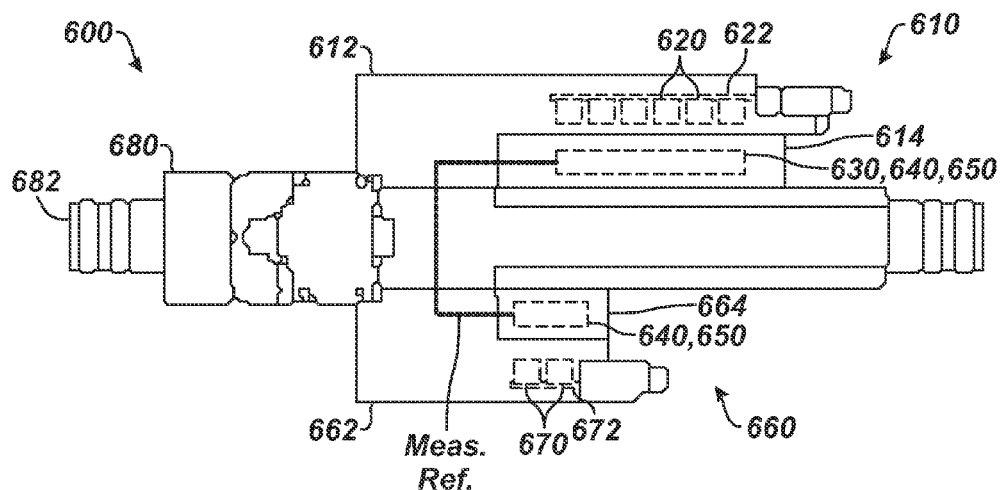
FIG. 15A illustrates a side view of a measurement device having a multi-channel source assembly and a detector unit.

In FIG. 15A, a side view of a measurement device 600 has a multi-channel source assembly 610 and a detector assembly 660 disposed on a flow body 680. For use in a downhole tool, the flow body 680 fits onto a tool chassis (not shown) that holds the flow body 680 in place and holds required electronics. In turn, the flow body 680 mates with a subassembly (not shown) that routes the flow buses in the downhole tool, and the tool chassis fits inside a tool housing (not shown) of the downhole tool. Fluid from one of the tool's fluid buses passes through a passage 682 from one end of the flow body 680 to the other end and passes by the source assembly 610 and detector assembly 660.

As shown, the sources assembly 610 can have housings 612/614 that couple to the flow body 680. One housing 612 holds the LED sources 620 arranged on a circuit board 622. The other housing 614 holds an arrangement of beam splitters and prisms (630, 640, 650), which are detailed below in FIG. 15B.

For its part, the detector assembly 660 can be similarly configured on the opposite side of the flow body 680. Accordingly, one housing 662 attached to the flow body 680 houses the photodiode detectors 670 disposed on a circuit board 672. Also, another housing 664 houses an arrangement of beam splitters and prisms (640, 650).

Signals for the measurement and reference channels issue from the source assembly 610 and pass to the detector assembly 660 using through-space optics (not shown). As disclosed herein, the reference channel can pass directly to the detector assembly 660, and the measurement channel can interact with fluid passing through the flow body 680 before passing to the detector assembly 660. Thus, the measurement channel may pass through a sample accessory (not shown), such as a sample cell or the like, in the flow body 680.

Figure 15B:
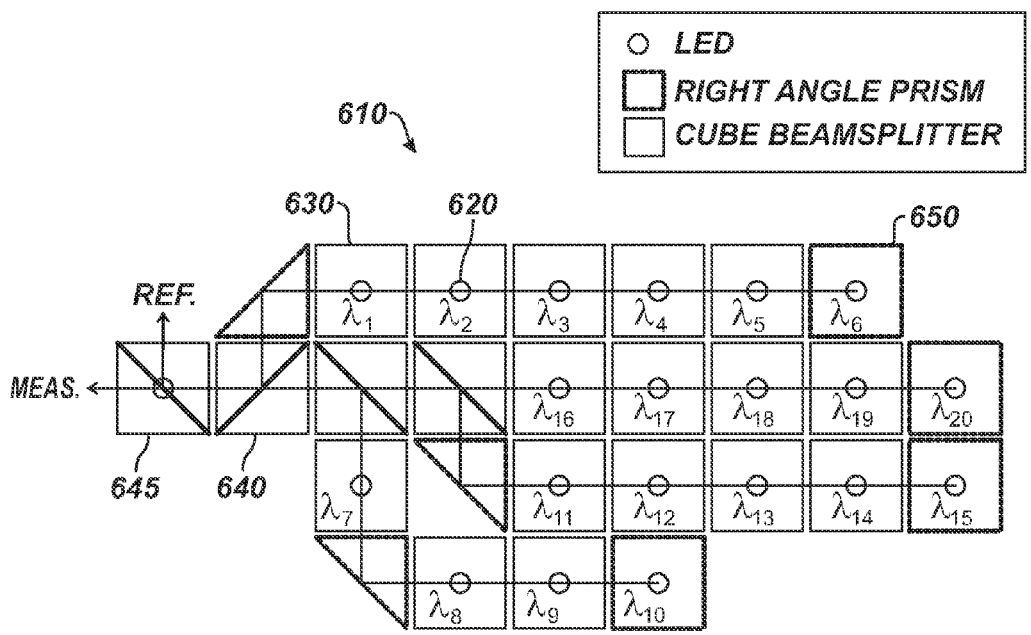
FIG. 15B diagrammatically illustrates arrangements for the source assembly and the detector units of the device in FIG. 15A.

Turning then to the plan schematic view in FIG. 15B, LED sources 620 for the source assembly 610 are arranged in a matrix or array pattern. Various cube beamsplitters 630, plate beamsplitters 640, and right angle prisms 650 route the input signals from the LEDs 620 to a final plate beamsplitter 645 that splits the input signal into a reference channel and a measurement channel as previously described. From the source assembly 610, both channels can be routed via fiber, mirrors, and the like to the detector assembly 660 with its photodiode detectors 670. For example, through-space optical approaches as well as fiber routing methods known to those in the art and disclosed herein can be used to route the channels.

As shown, this source assembly 610 has twenty LEDS 620 and several beamsplitters 640/650 configured for particular wavelengths. The measurement wavelengths and LED center wavelengths $\lambda_1$ to $\lambda_{20}$ can be selected to cover the spectral channels suitable for downhole real-time analysis of crude or other downhole fluids. Likewise, longpass filter specifications can be selected for the measurement wavelengths and LED center wavelengths used. In one example, the source assembly 610 is configured for measurement wavelengths in the visible and near infrared spectral regions. As one skilled in the art will appreciate, the number of LEDs 620 and beamsplitters 640/650 as well as the subject wavelengths and other values can be configured for a particular implementation.

G. Control Circuitry

Figure 16:
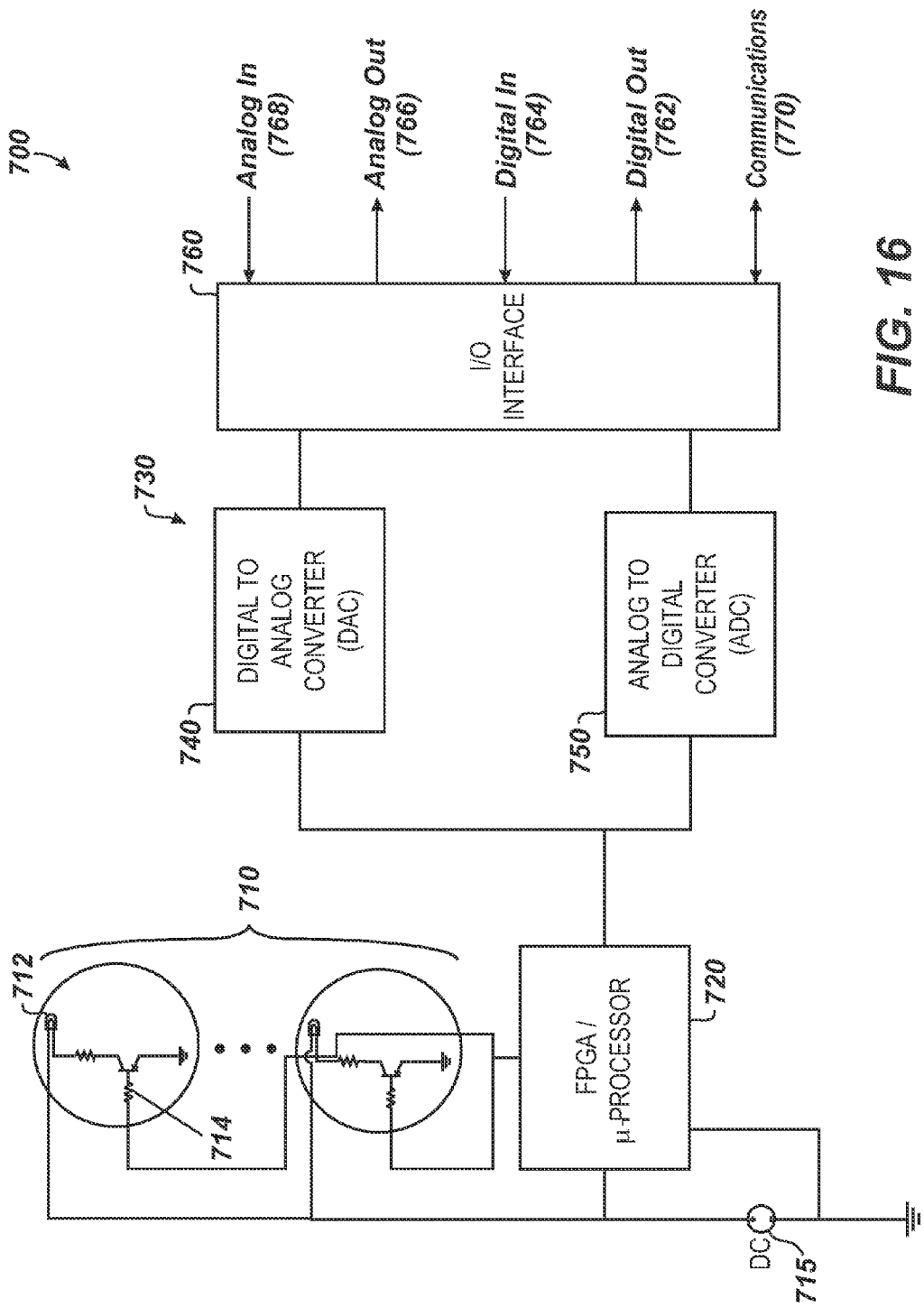
FIG. 16 schematically illustrates control circuitry for the disclosed multi-channel source assembly.

As discussed previously in FIG. 3A-3B, the source assembly 100 uses control circuitry 160 to control the sources in the source/coupler unit 110. FIG. 16 schematically illustrates one implementation of control circuitry 700 for the disclosed source assembly. The control circuitry 700 has processing circuitry 720 coupled to a source unit 710, conversion circuitry 730, and an input/output interface 760. As shown here, the source unit 710 has multiple LEDs 712, but could have other sources as disclosed herein.

The processing circuitry 720 uses programmable control schemes to control operation of the source assembly 710 and can have a microprocessor or Field-Programmable Gate Array (FPGA). In operation, the processing circuitry 720 drives the LEDs 712, sets the individual modulation frequencies for the LEDs 712, and performs other control functions discussed below. To drive the LEDs 712, the processing circuitry 720 controls the power from a DC power source 715 to the LEDs 712 using control signals communicated to transistors 714. Furthermore, the source assembly hardware 710 may be adjusted providing fixed unique amplitudes for each LED source 712. In addition, the processor 720 may control LED source amplitude (i.e., intensity) through pulse width modulation or other means.

In driving the LEDs 712, the processing circuitry 720 can modulate each of the sources at an independent frequency. To modulate the LEDs 712, for example, the processing circuitry 720 can turn each of the individual sources 712 on and off, modulate each of the individual sources 712 about a mean frequency, or modulate one or more of the individual sources 712 at the same frequency. In general, the frequency modulation can be in a range between 1 and 20-kHz, depending on the measurement requirements by the operational mode used (i.e., either raster scanning, FFT analysis, etc. as described below).

The input/output interface 760 has several inputs and outputs, such as a digital/trigger output 762, a digital/trigger input 764, one or more analog outputs 766, one or more analog inputs 768, and a communications interface (770). The outputs 762/766/770 of the interface 160 can be used for sending messages to other systems, such as sending status messages about the operation of the source assembly, health of the sources 712, etc.

These inputs and outputs of the interface 760 can be used to interact with external control circuitry of a detection system (not shown) for external control of the control circuitry 700. For example, either the analog input 768 or communications interface 770 can receive control signals used for manual or automated control of the circuitry's operation. This external control can be from an external source, such as surface equipment or from a separate downhole controller. When received, the control signals can configure the control circuitry's operation to account for variable conditions, such as a change in temperature, a change in fluid to be analyzed, a change in desired mode of operation to be used, etc. The external control can also operate the control circuitry 700 to handle events that require exact timing by using the trigger output 762 and input 764 for triggering signals.

In addition to external control, control circuitry 700 can use data from the analog input 768 as part of an automated control scheme. The conversion circuitry 730 interposed between the processing circuitry 720 and the input/output interface 760 uses analog-to-digital conversion (ADC) to convert analog signals from the analog input 768 into digital signals for the processing circuitry 720 to process. These analog signals can include amplitude measurements used for feedback or can include analog control signals for manual or automated control of the circuitry's operation.

In one example, either the analog input 768 or a communications interface 770 can receive control signals from the external control circuitry (not shown) based on the reference channel amplitude and can use these inputs to control the operation of the sources 712. In such a situation, the amplitude measurements can come from a detection system (not shown) configured to detect optical signals of the reference channel (150). Using those amplitude measurements as feedback, the control circuitry 700 can then control the individual sources 712. For example, the control circuitry 700 can maintain a more uniform intensity profile for the LEDs 712 even when there are significant changes in environmental conditions. To do this, the processing circuitry 720 can drive the LEDs 712 to maintain a relatively flat illumination profile across the entire temperature range by using pulse width modulation or other methods of the drive signals for the LEDs 712.

In addition to controlling the LED sources 712 as shown, it will be appreciated that the control circuitry 700 can include electronic components to illuminate sources other than LEDs and to operate a scanning optic (as in FIG. 3B). The control circuitry 700 can function on its own independent of any measurements made by a detection unit (not shown), such as disclosed in incorporated co-pending application Ser. No. 12/613,808 entitled "Multi-Channel Detector Assembly for Downhole Spectroscopy." Although analog control is discussed using analog input 768, the control circuitry 700 can use a digital input 764 to receive digital control signals. In addition, the control circuitry's interface 760 can include additional inputs and outputs, such as an analog output for sending signals to another downhole controller or for sending signals to a telemetry unit to relay to surface equipment. For this reason, the control circuitry 700 may include a digital-to-analog convertor circuit 740 and an analog-to-digital convertor circuit 750.

H. Operational Modes

In performing spectroscopy downhole, the multi-channel source assembly 100 (FIGS. 3A-3B) can be operated using one or more modes that can give operators control over scan speed, signal-to-noise ratio, and process monitoring methodology. For the current explanation, the operational modes are described in terms of the embodiment of the source assembly 100 having control circuitry 700 and all LED sources 712 as in FIG. 16. However, one skilled in the art will appreciate that the disclosed operational modes can be modified for any other source assemblies disclosed herein.

For analysis purposes, the reference channel (150) can be spectrally correlated with the measurement channel (140) so that the data is properly scaled (i.e., calibrated) as discussed previously. In doing this, the source assembly's control circuitry 700 in conjunction with sample and detection units (not shown) can analyze a sample's spectral properties (i.e. absorption, transmission, etc.) using channels (140/150) via raster scanning in continuous wave (CW) mode, raster scanning in modulated mode with lock-in detection, or simultaneous modulation with Fast-Fourier Transform (FFT) analysis or other optical transform approach to spectrally deconvolve the simultaneously modulated sources 712. In addition to these modes, each source 712 can be driven at different current levels to control amplitude, which in-turn can improve signal-to-noise within weak or highly attenuating optical bands.

In general, the operational modes for the source assembly 100 can be implemented as software or the like in the control circuitry 700. Depending on the implementation, the source assembly's hardware components (FPGA, ADC, multiplexers, sources, etc.) can be specifically configured to operate under one of the particular modes. The source assembly's hardware is configured to operate under all of these different modes. In this way, operating the source assembly 100 in one of the desired modes may simply require programmable changes to the control circuitry 700, which can occur during installation or even during downhole use.

1. Synchronous Encoding

In one operational mode, the control circuitry 700 operates the sources 712 using synchronous encoding. In this mode, the control circuitry 700 operates each source 712, or a limited subset of sources 712, simultaneously with each source 712 being modulated at a unique, independent frequency. The modulation frequencies used should not share common higher order harmonics.

In one example of this mode, the control circuitry 700 illuminates all LED sources 712 at the same time and modulates the LED sources 712 at unique, independent frequencies. Operating in this mode allows the measurements signals to be spectrally de-convolved using fast Fourier transform (FFT) analysis to produce information for later data processing. In this mode, the analog to digital sampling rate is used to set the frequency resolution.

In an alternative but similar mode, the control circuitry 700 illuminates the sources 712 using a set of fixed frequencies that have predefined properties. In particular, the control circuitry 700 pulses the LED sources 712 simultaneously using fixed frequency increments, and the control circuitry 700 uses waveforms to pulse the LED sources 712 that are based on an integer number of cycles. Operating in this mode allows the measurement signals to be spectrally de-convolved using a predefined numerical method based on the known temporal characteristics of the waveform to produce information for later data processing. Ideally, the signal phase shift relative to the modulation frequency is preferably very small. In addition, the minimum sample period used in the analysis is preferably greater than $1/\Delta f$, where $\Delta f$ is the frequency increment above the fundamental frequency ($f_0$) used to illuminate the individual LED sources 712. Finally, no odd multiples of f (i.e. 1 kHz and 3 kHz) are used to pulse the LED sources 712.

2. Asynchronous Encoding

In another operational mode, the control circuitry 700 operates the sources 712 using asynchronous encoding. Here, the control circuitry 700 operates each source 712, or a limited subset of sources 712, in a serial fashion with only one source illuminated at any point in time. In this mode, for example, each LED source 712 in the unit 710 is illuminated sequentially one at a time so that raster scanning can be performed on the signals produced. Alternatively, each LED source 712 in the unit 710 is illuminated sequentially one at a time with each LED source 712 being oscillated at a fixed frequency common to all the LED sources 712. This enables raster scanning with lock-in detection to be performed.

3. Asynchronous Hadamard Transform Encoding

In yet another operational mode, the control circuitry 700 operates the sources 712 using asynchronous Hadamard Transform encoding. In this mode, the control circuitry 700 operates a unique sequence of a subset of sources 712 in a cyclic fashion with only one subset of sources in operation at a given point in time. While operating in this mode, each source 712 is modulated at the same frequencies.

I. Source Selection

As discussed above, the disclosed source assembly can use various types of sources to operate across a large band of EM wavelengths used for spectral analysis. The EM wavelengths can be in the x-ray, gamma, ultraviolet, visible, or infrared range or be in any combination of these ranges. Such EM radiation has been referred to herein as light or optical signals. Examples of suitable sources that meet at least some of the previously discussed specifications for downhole use include multi-channel solid state light emitting diodes (LED), super-luminescent light emitting diodes (SLED), or laser diodes (LD) where each of the individual sources have been coupled using a fiber bundle, a fiber coupler such as a star coupler, a bulk optical coupler, or other coupler as disclosed herein.

In one implementation, each of the sources for the disclosed assembly is an LED. Depending on the LED's characteristics and the intended application, these LEDs may or may not use bandpass filters. Using LEDs to define the measurement wavelengths allows the disclosed source assembly to be made both compact and versatile in addition to maximizing optical throughput across a broad spectral range. In addition, by using the optical filters, LEDs with broad spectral profiles can be used with desired wavelengths that are relatively close together for performing spectroscopy. This is especially useful for the near-infrared (NIR) region where a large amount of information in molecular absorbance data occurs for hydrocarbons, water, and reservoir gases. For example, a single type of LED can be used to provide source light for 3 or 4 specific bands, since the LEDs can be separately filtered for each wavelength measurement of interest with a suitable spectral filter. This enables the disclosed source assembly to meet measurement requirements for particular implementations.

Although the disclosure refers to electromagnetic radiation using the terms "optical signals," "light," "emissions," and the like, these references may actually be intended to include wavelengths outside the bounds of visible light. Further, while the discussion herein focused on the wavelength ranges of the ultraviolet, visible, and near-infrared regions of the electromagnetic spectrum being used, it will be appreciated that the disclosed device can be configured to manipulate all wavelengths of electromagnetic radiation. As used herein, the term "spectroscopy" refers to the production and investigation of spectra and the term "spectroscopic devices" includes instruments for forming and examining spectra especially in the visible region of the electromagnetic spectrum including, but is not limited to, a spectrometer, among other instruments for spectral analysis of downhole fluids.

The foregoing description of preferred and other embodiments is not intended to limit or restrict the scope or applicability of the inventive concepts conceived of by the Applicants. In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A source assembly for downhole spectroscopy, comprising:
    a plurality of individual light emitting diode (LED) sources deployed downhole in the source assembly and generating optical signals across a spectral range of wavelengths;
    a routing assembly deployed downhole in the source assembly, the routing assembly spectrally filtering the generated signals of the LED sources, combining the spectrally filtered signals into a combined signal, and routing the combined signal into a reference channel and one or more measurement channels; and
    control circuitry deployed downhole in the source assembly, the control circuitry electrically coupled to the LED sources and operable to electronically modulate each of the LED sources at an independent frequency.

2. The assembly of claim 1, wherein the LED sources are selected from the group consisting of light emitting diodes (LEDs) and super-luminescent light emitting diodes (SLEDs).

3. The assembly of claim 1, wherein the LED sources provide a continuous spectral distribution over a broad spectral range of wavelengths.

4. The assembly of claim 1, wherein the LED sources provide a non-continuous spectral distribution of two or more spectrally continuous regions interposed by at least one spectrally dark region over a broad spectral range of wavelengths.

5. The assembly of claim 1, wherein the routing assembly comprises one or more filters spectrally filtering the optical signals from one or more of the LED sources.

6. The assembly of claim 1, wherein the routing assembly comprises one or more optical elements spatially shaping the optical signals from one or more of the LED sources.

7. The assembly of claim 1, wherein to electronically modulate each of the LED sources, the control circuitry turns each of the individual LED sources on and off or electronically modulates each LED source about a mean amplitude.

8. The assembly of claim 1, wherein to electronically modulate each of the LED sources, the control circuitry electronically modulates one or more of the individual LED sources at a unique frequency different from one another.

9. The assembly of claim 1, wherein to electronically modulate each of the LED sources, the control circuitry electronically modulates one or more of the individual LED sources at the same frequency.

10. The assembly of claim 1, wherein the routing assembly comprises:
    one or more couplers optically coupled to each of the LED sources; and
    a router coupled to the one or more couplers and routing the optically combined signal from the one or more couplers into the reference channel and the one or more measurement channels.

11. The assembly of claim 10, wherein the one or more couplers comprise optical fibers, each of the LED sources imaged into one of the optical fibers, each of the fibers bundled together into a fiber bundle optically coupled to the router.

12. The assembly of claim 10, wherein the one or more couplers comprise optical fibers optically coupled to the LED sources, each of the LED sources imaged into one of the optical fibers, one or more of the optical fibers fused with another of the optical fibers using a tree coupling topology, wherein output of the tree coupling topology is optically coupled to the router.

13. The assembly of claim 10, wherein the one or more couplers comprise a segmented mirror having the LED sources arranged thereabout, the segmented mirror imaging optical signals from each of the LED sources into the combined signal that is optically coupled to the router.

14. The assembly of claim 10, wherein the one or more couplers comprises a series of filters disposed adjacent the LED sources and at least one optic element imaging at least a portion of the optical signals from each of the adjacent LED sources to the combined signal optically coupled to the router.

15. The assembly of claim 1, wherein the routing assembly comprises an adaptive optical element optically coupled to the combined signal and oscillating between a first orientation and one or more second orientations, the adaptive optical element in the first orientation producing the reference channel, the adaptive optical element in the one or more second orientations producing the one or more measurement channels.

16. The assembly of claim 1, wherein the LED sources are spatially configured on an array topology arranged in one or more dimensions, and wherein the routing assembly comprises a grating optically coupled to the spatially configured LED sources and combining the signals from the LED sources into at least one optical beam.

17. The assembly of claim 16, wherein the routing assembly comprises a router optically coupled to the at least one optical beam and routing the at least one optical beam into the reference channel and the one or more measurement channels.

18. The assembly of claim 16, wherein the at least one optical beam comprises first and second optical beams, the first optical beam generated using a first order reflection of the grating, the second optical beam generated using a second order reflection of the grating, the one or more measurement channels imaged using the first order reflection, the reference channel imaged using the second order reflection.

19. The assembly of claim 1, wherein the control circuitry receives input indicative of measured energy of the reference channel and controls an amplitude of the LED sources based on the input.

20. The assembly of claim 1, wherein the control circuitry electronically modulates the LED sources in a synchronous encoding mode in which the control circuitry operates each of two or more LED sources simultaneously using an independent frequency to generate optical signals, the synchronous encoding mode enabling Fast-Fourier Transform analysis of the measurement and reference channels.

21. The assembly of claim 1, wherein the control circuitry electronically modulates the LED sources in a synchronous encoding mode in which the control circuitry operates the LED sources simultaneously using fixed frequency increments, the synchronous encoding mode enabling deconvolution of the measurement and reference channels based on predefined temporal characteristics of the fixed frequency increments.

22. The assembly of claim 1, wherein the control circuitry electronically modulates the LED sources in an asynchronous encoding mode in which the control circuitry operates each of two or more LED sources in a serial fashion with only one of the LED sources in operation at any point in time, the asynchronous encoding mode enabling raster scanning analysis of the measurement and reference channels.

23. The assembly of claim 1, wherein the control circuitry electronically modulates the LED sources in an asynchronous encoding mode in which the control circuitry operates a unique sequence of subsets of the sources in a cyclic fashion with only one of the subsets of the LED sources in operation at a given point in time, the asynchronous encoding mode enabling Hadamard Transform analysis of the measurement and reference channels.

24. A downhole fluid analysis tool, comprising:
 a tool housing deployable downhole and having a flow passage for a fluid sample; and
 a fluid analysis device disposed in the tool housing relative to the flow passage,
  the fluid analysis device at least including—
   a plurality of individual light emitting diode (LED) sources generating optical signals across a spectral range of wavelengths,
   a routing assembly spectrally filtering the generated signals, optically combining the spectrally filtered signals of each of the LED sources into a combined signal, and routing the combined signal into a reference channel and one or more measurement channels, and
   control circuitry electrically coupled to the LED sources and operable to electronically modulate each of the LED sources at an independent frequency.

25. A downhole fluid analysis method, comprising:
 deploying a fluid analysis device downhole;
 obtaining a fluid sample downhole;
 generating a plurality of optical signals across a spectrum of wavelengths by electronically modulating each of a plurality of light emitting diode (LED) sources at an independent frequency;
 spectrally filtering the generated signals from one or more of the LED sources;
 combining the spectrally filtered signals into a combined signal; and
 routing the combined signal concurrently into one or more measurement channels for interacting with the fluid sample and into a reference channel for dynamically scaling the measurement channel.

26. The method of claim 25, wherein spectrally filtering the generated signals from one or more of the LED sources comprises concurrently routing the spectrally filtered signals from one or more of the LED sources using an arrangement of optical elements.

27. The method of claim 25, wherein modulating each of the LED sources comprises turning each of the individual LED sources on and off.

28. The method of claim 25, wherein modulating each of the LED sources comprises modulating each of the individual LED sources about a mean amplitude.

29. The method of claim 25, wherein modulating each of the LED sources comprises modulating one or more of the individual LED sources at the same frequency.

30. The method of claim 25, wherein modulating each of the LED sources comprises modulating one or more of the individual LED sources at unique frequencies different from one another.

31. The method of claim 25, wherein combining the spectrally filtered signals into a combined signal comprises imaging each of the individual LED sources into an optical coupler.

32. The method of claim 25, wherein routing the combined signal comprises fractionally splitting the combined signal into the reference and measurement channels.

33. The method of claim 25, wherein routing the combined signal comprises oscillating the combined signal between a first orientation producing the reference channel and a second orientation producing the measurement channel.

34. The method of claim 25, wherein the acts of generating, combining, and routing comprise:
 spatially configuring the individual LED sources in one or more dimensions;
 combining the optical signals from the spatially configured sources using a grating; and
 routing the combined signal into the measurement and reference channels.

35. The method of claim 34, wherein routing the combined signal comprises imaging a first portion of the combined signal into the reference channel and imaging a second portion of the combined signal into the one or more measurement channels.

36. The method of claim 25, wherein modulating each of a plurality of LED sources is controlled based on measured energy of the reference channel.

37. The method of claim 25, wherein modulating each of a plurality of LED sources comprises synchronously encoding the LED sources by simultaneously operating each of two or more of the LED sources and modulating each with an independent frequency.

38. The method of claim 25, wherein modulating each of a plurality of LED sources comprises synchronously encoding the LED sources by operating the LED sources simultaneously using fixed frequency increments.

39. The method of claim 25, wherein modulating each of a plurality of LED sources comprises asynchronously encoding the LED sources by operating each of two or more of the LED sources in a serial fashion with only one of the LED sources in operation at any point in time.

40. The method of claim 25, wherein modulating each of a plurality of LED sources comprises asynchronously encoding the sources by operating a unique sequence of subsets of the LED sources in a cyclic fashion with only one of the subsets of the LED sources in operation at a given point in time.

41. The apparatus of claim 10,
wherein the one or more couplers comprise:
spectral filters disposed adjacent the LED sources, and
optic elements disposed adjacent the LED sources and imaging at least a portion of the spectrally filtered optical signals from the adjacent LED sources to the combined signal optically coupled to the router; and
wherein the router comprises a beam splitter fractionally splitting the combined signal into the reference and measurement channels.

42. The apparatus of claim 14, wherein the filters are thermally stable for downhole conditions in which the source assembly deploys.

43. The assembly of claim 1, wherein the routing assembly comprises a splitter fractionally splitting the combined signal into the reference and the one or more measurement channels.

44. The apparatus of claim 32, wherein fractionally splitting the combined signal into the reference and measurement channels comprises splitting the combined signal into the reference channel disproportionally compared to the measurement channel.

45. The assembly of claim 1, wherein the routing assembly comprises a micro-optical bench.

46. The apparatus of claim 43, wherein the splitter splits the combined signal into the reference channel disproportionately compared to the one or more measurement channels.

47. The assembly of claim 16, wherein the routing assembly images a first portion of the at least one optical beam into a first optic fiber for the reference channel and images one or more second portions of the at least one optical beam into one or more second optic fibers for the one or more measurement channels.

48. The method of claim 34, wherein the acts of routing comprises:
routing a first order reflection of the grating into the one or more measurement channels; and
routing a second order reflection of the grating into the reference channel.

49. A source assembly for downhole spectroscopy, comprising:
a plurality of individual sources generating optical signals across a spectral range of wavelengths and spatially configured on an array topology arranged in one or more dimensions;
a routing assembly having a grating optically coupled to the generated signals of the spatially configured sources, the routing assembly routing a first order reflection of the generated signals on the grating to one or more measurement channels and routing a second order reflection of the generated signals on the grating to a reference channel; and
control circuitry electrically coupled to the sources and operable to electronically modulate each of the sources at an independent frequency.

50. A downhole fluid analysis method, comprising:
deploying a fluid analysis device downhole, the fluid analysis device having a plurality of individual sources spatially configured in one or more dimensions;
obtaining a fluid sample downhole;
generating a plurality of optical signals across a spectrum of wavelengths by electronically modulating each of the sources at an independent frequency;
optically coupling a grating to the generated signals of the spatially configured sources;
routing a first order reflection of the generated signals on the grating to one or more measurement channels for interacting with the fluid sample; and
routing a second order reflection of the generated signals on the grating to a reference channel for dynamically scaling the measurement channel.

* * * * *